(12) United States Patent
Benenson et al.

(10) Patent No.: US 10,793,921 B2
(45) Date of Patent: Oct. 6, 2020

(54) LOW-LEAKAGE CELLULAR BIOSENSOR SYSTEM

(71) Applicant: ETH ZURICH, Zurich (CH)

(72) Inventors: Yaakov Benenson, Basel (CH); Nicolas Lapique, Villars-Tiercelin (FR)

(73) Assignee: ETH ZURICH, Zurich (CH)

( * ) Notice: Subject to any disclaimer, the term of this patent is extended or adjusted under 35 U.S.C. 154(b) by 0 days.

(21) Appl. No.: 15/316,512

(22) PCT Filed: Jun. 4, 2015

(86) PCT No.: PCT/EP2015/062507
§ 371 (c)(1),
(2) Date: Dec. 5, 2016

(87) PCT Pub. No.: WO2015/185691
PCT Pub. Date: Dec. 10, 2015

(65) Prior Publication Data
US 2017/0159135 A1    Jun. 8, 2017

(30) Foreign Application Priority Data

Jun. 5, 2014 (EP) .................................... 14001960

(51) Int. Cl.
| | | |
|---|---|---|
| C12Q 1/68 | (2018.01) | |
| C12Q 1/6897 | (2018.01) | |
| G01N 33/50 | (2006.01) | |
| C12N 15/63 | (2006.01) | |
| C12N 15/10 | (2006.01) | |

(52) U.S. Cl.
CPC .......... *C12Q 1/6897* (2013.01); *C12N 15/10* (2013.01); *C12N 15/63* (2013.01); *G01N 33/5008* (2013.01)

(58) Field of Classification Search
None
See application file for complete search history.

(56) References Cited

U.S. PATENT DOCUMENTS

| | | | | |
|---|---|---|---|---|
| 2010/0175141 | A1* | 7/2010 | Collins | C12N 15/111 800/13 |
| 2013/0034907 | A1* | 2/2013 | Collins | C12N 15/63 435/455 |
| 2013/0202532 | A1* | 8/2013 | Benenson | C12Q 1/6897 424/9.1 |

OTHER PUBLICATIONS

International Report on Patentability for PCT/EP2015/062507, dated Dec. 6, 2016.
Sektas M et al: "Tightly Controlled Two-Stage Expression Vectors Employing the FLP/FRT-Mediated Inversion of Cloned Genes", Molecular Biotechnology, Humana Press, Inc, US, vol. 9, No. 1, Feb. 1, 1998 (Feb. 1, 1998), pp. 17-24, XP001034234.
Sektas M et al: "Expression plasmid with a very tight two-step control: Int/att-mediated gene inversion with respect to the stationary promoter", Gene, Elsevier, Amsterdam, NL, vol. 267, No. 2, Apr. 18, 2001 (Apr. 18, 2001), pp. 213-220, XP004235034, ISSN: 0378-1119, DOI: 10.1016/S0378-1119(01)00395-X abstract; p. 215-216, para. 3.1; p. 218, para. 3.3; fig. 1, 2; table 2.
Alec Ak Nielsen et al: "Advances in genetic circuit design: novel biochemistries, deep part mining, and precision gene expression", Current Opinion in Chemical Biology, vol. 17, No. 6, Dec. 1, 2013 (Dec. 1, 2013), pp. 878-892, XP055204329, ISSN: 1367-5931, DOI: 10.1016/j.cbpa.2013.10.003 the whole document.
Yaakov Benenson: "Biomolecular computing systems: principles, progress and potential", Nature Reviews Genetics, vol. 13, No. 7, Jun. 12, 2012 (Jun. 12, 2012), pp. 455-468, XP055107191, ISSN: 1471-0056, DOI: 10.1038/nrg3197 the whole document.
Piro Siuti et al: "Synthetic circuits integrating logic and memory in living cells", Nature Biotechnology, vol. 31, No. 5, Feb. 10, 2013 (Feb. 10, 2013), pp. 448-452, XP055204650.
International Search Report and Written Opinion of the International Searching Authority, dated Aug. 10, 2015, for PCT/EP2015/062507, filed Jun. 4, 2015.
Nicolas Lapique et al: "Digital switching in a biosensor circuit via programmable timing of gene availability", Nature Chemical Biology, vol. 10, No. 12, Oct. 14, 2014 (Oct. 14, 2014), pp. 1020-1027, XP055203883, ISSN: 1552-4450, DOI: 10.1038/nchembi0.1680 the whole document.
Laura Prochazka et al: "Highly modular bow-tie gene circuits with programmable dynamic behaviour", Nature Communications, vol. 5, Oct. 14, 2014 (Oct. 14, 2014), p. 4729, XP055203938.
Atasoy et al., "A FLEX Switch Targets Channelrhodopsin-2 to Multiple Cell Types for Imaging and Long-Range Circuit Mapping," The Journal of Nueroscience, 2008, vol. 28, No. 28 pp. 7025-7030.

(Continued)

*Primary Examiner* — Catherine S Hibbert
(74) *Attorney, Agent, or Firm* — Bryan D. Zerhusen, Esq.; Nicholas R. Herrel, Esq.; Cantor Colburn LLP

(57) ABSTRACT

The present invention is directed to a cellular biosensor system comprising (A) a repressor module comprising one or more genes, which in their cumulative gene action exert repressing and/or inhibitory effect(s) on (B), an output module comprising at least one gene comprising at least one output sequence generating one or more output signals (i) in the absence of repressing and/or inhibitory effect(s) of the repressor module (A) and (ii) in the presence of at least one recombinase expressed by (C), a recombinase module comprising at least one gene comprising at least one sequence encoding a site-specific recombinase that enables gene rearrangement in the output module resulting in one or more output signals in the absence of repressing and/or inhibitory effect(s) of the repressor module, wherein the repressing and/or inhibitory effects of the repressor module are controlled by one or more inputs that negatively affect the repressing and/or inhibitory effects of the repressor module (A). In addition, the present invention relates a biosensor network comprising the cellular biosensor system of the present invention and their uses in the diagnosis of a disease, for drug discovery, for biomanufacturing methods, for producing a transgenic animal, and for methods for the identification or classification of a cell status.

Figure 1:
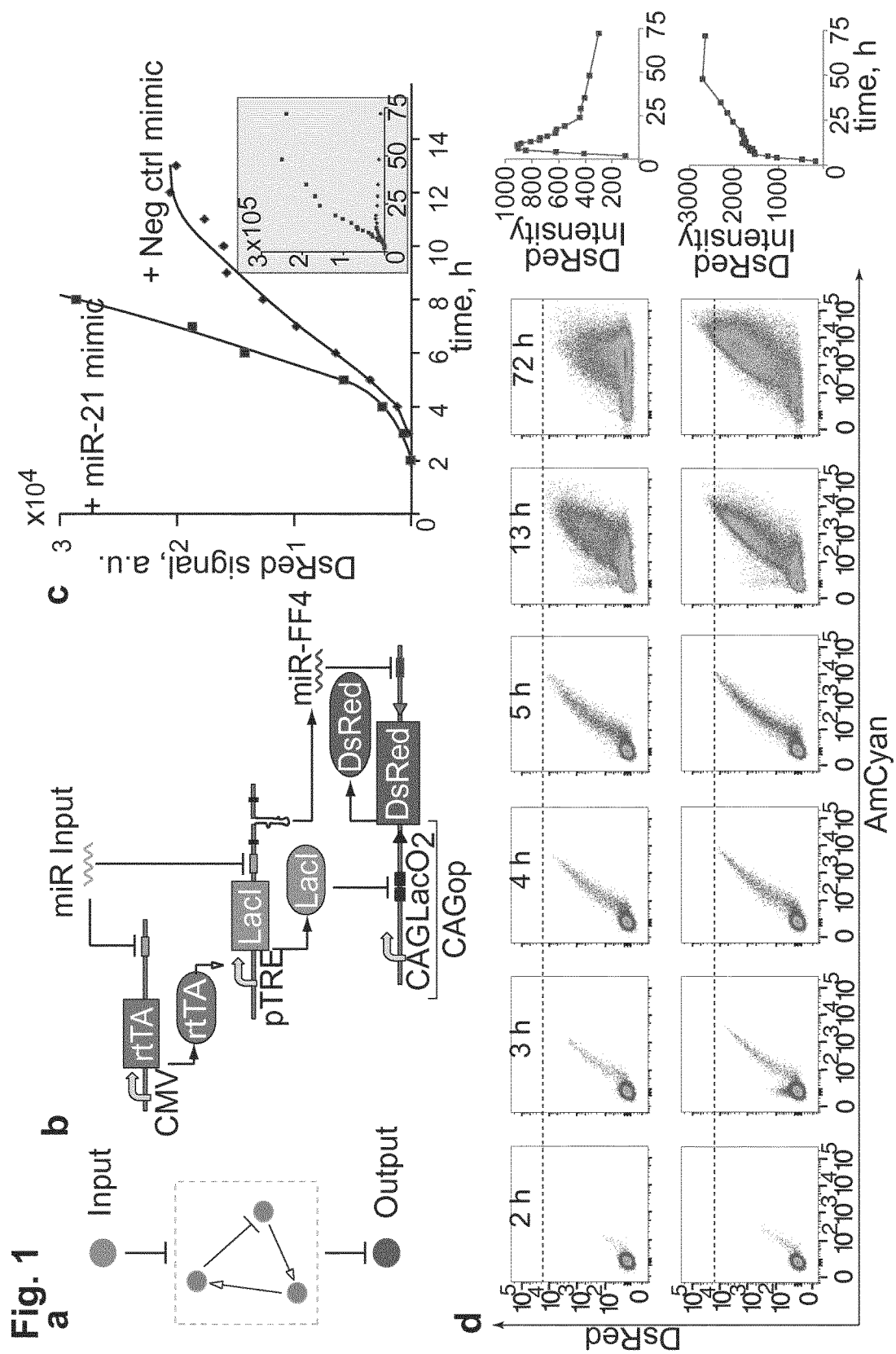

40 Claims, 13 Drawing Sheets
Specification includes a Sequence Listing.

(56) References Cited

OTHER PUBLICATIONS

Backman et al., "Use of Synchronous Site-Specific Recombination in Vivo to Regukate Gene Expression", Nature, 1984, pp. 1045-1049.
Benenson; "Biomolecular computing systems: principles, progress and potential", Nature Reviews, 2012, vol. 13, pp. 455-469.
Bonnet et al., "Amplifying Genetic Logic Gates", Science Magazine, 2013, vol. 340, pp. 599-604.
Callura et al., "Tracking, tuning, and terminating microbial physiology using synthetic riboregulators," PNAS, 2010, vol. 107, No. 36, pp. 15898-15903.
Dale et al., "Gene transfer with subsequent removal of the selection gene from the host genome," Applied Biological Sciences; Proc. Natl. Acad. Sci., 1991, vol. 88, pp. 10558-10562.
Deans et al., "A Tunable Genetic Switch Based on RNAi and Repressor Proteins for Regulating Gene Expression in Mammalian Cells," Cell, 2007, vol. 130, pp. 363-372.
Dunlop et al., "Regulatory activity revealed by dynamic correlations in gene expression noise," Nature Genetics, 2008, vol. 40, No. 12, pp. 1493-1498.
Elowitz et al., "A synthetic oscillatory network of transcriptional regulators," Nature, 2000, vol. 403, pp. 335-338.
Eroshenko et al., "Mutants of Cre recombinase with improved accuracy," Nature Communications, 2013, pp. 1-10.
Friedland et al., "Synthetic Gene Networks That Count," Science Magazine, 2009, vol. 324, pp. 1199-1202.
Gardner et al., "Construction of a genetic toggle switch in *Escherichia coli*," Nature, 2000, vol. 403, pp. 339-342.
Greber et al., "Mammalian synthetic biology: Engineering of sophisticated gene networks," Journal of Biotechnology, 2007, vol. 130, pp. 329-345.
Grindley et al., "Mechanisms of Site-Specific Recombination," Ann. Rev. Biochem., 2006, pp. 567-600.
Ham et al., "Design and Construction of a Double Inversion Recombination Switch for Heritable Sequential Genetic Memory," PLos One, 2008, vol. 3, Issue 7, pp. 1-9.
Hansen et al., "Transplantation of prokaryotic two-component signaling pathways into mammalian cells," PNAS, 2014, vol. 111, No. 44, pp. 15705-15710.
Haynes et al., "A Sensitive Switch for Visualizing Natural Gene Silencing in Single Cells," ACS Synthetic Biology, 2012, vol. 1, pp. 99-106.
Indra et al., "Temporally-controlled site-specific mutagenesis in the basal layer of the epidermis: comparison of the recombinase activity of the tamoxifen-inducible Cre-ERt and the Cre-ERt2 recombinases," Nucleic Acids Research, 1999, vol. 27, No. 22, pp. 4324-4327.
Mansfield et al., "MicroRNA-responsive 'sensor' transgenes uncover Hox-like and other developmentally regulated patterns of vertebrate microRNA expression," Nature Genetics, 2004, vol. 36, No. 10, pp. 1079-1083.
Mukherji et al., "Synthetic biology: understanding biological design from synthetic circuits," Nature Reviews: Genetics, 2009, vol. 10, 859-871.
Rinaudo et al.,"A universal RNAi-based logic evaluator that operates in mammalian cells," Nature Biotechnology, 2007, vol. 25, No. 7, pp. 795-801.
Schnutgen et al., "A directional strategy for monitoring Cre-mediated recombination at the cellular level in the mouse," Nature Biotechnology, 2003, vol. 21, pp. 562-565.
Siegert et al., "Transcriptional code and disease map for adult retinal cell types," Nature Nueroscience, 2012, vol. 15, No. 3, pp. 487-497.
Siuti et al., "Synthetic circuits integrating logic and memory in living cells," Nature Biotechnology, 2013, vol. 31, No. 5, pp. 448-453.
Stanton et al., "Systematic Transfer of Prokaryotic Sensors and Circuits to Mammalian Cells," American Chemical Society, 2014, vol. 3, pp. 880-891.
Weber et al., "A synthetic mammalian gene circuit reveals antituberculosis compounds," PNAS, 2008, vol. 105, No. 29, pp. 9994-9998.
Xie et al., "Multi-input RNAi-Based Logic Circuit for Identification of Specific Cancer Cells," Science, 2011, vol. 333, pp. 1307-1311.
Zhang et al., "Design of a dynamic sensor-regulator system for production of chemicals and fuels derived from fatty acids," Nature Biotechnology, 2012, vol. 30, No. 4, pp. 354-359.

* cited by examiner

Fig. 2
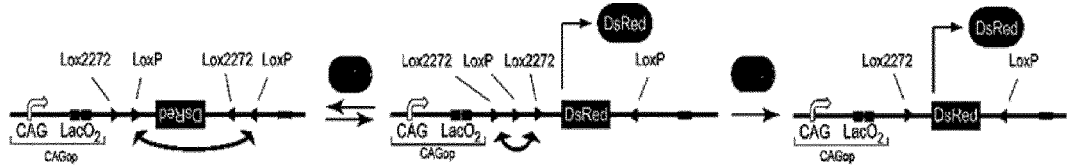
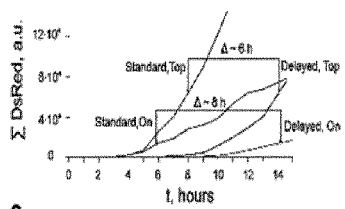
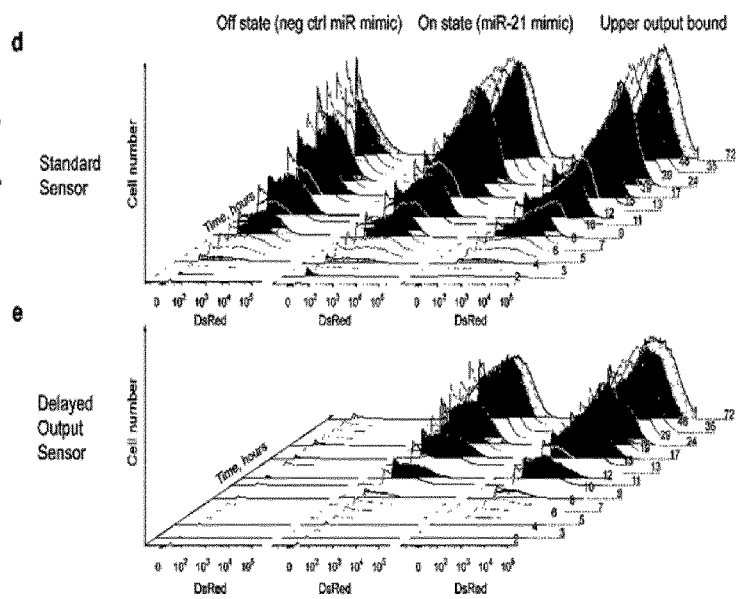
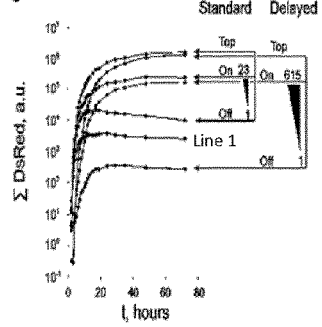
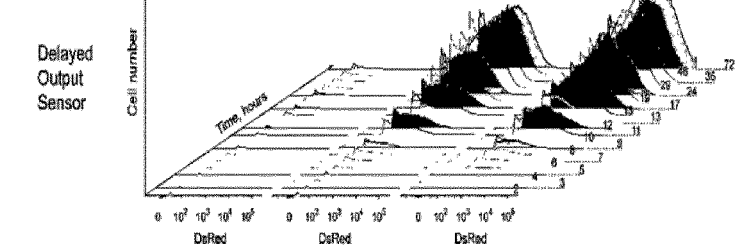
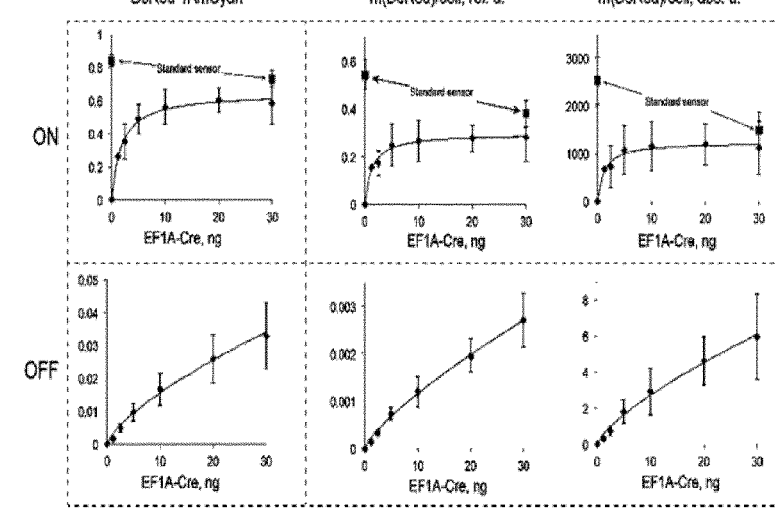
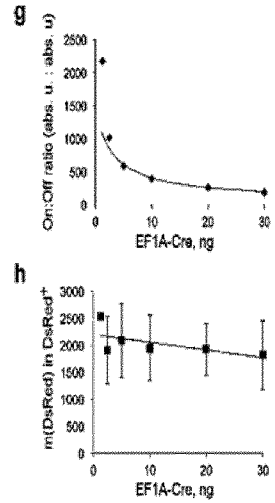

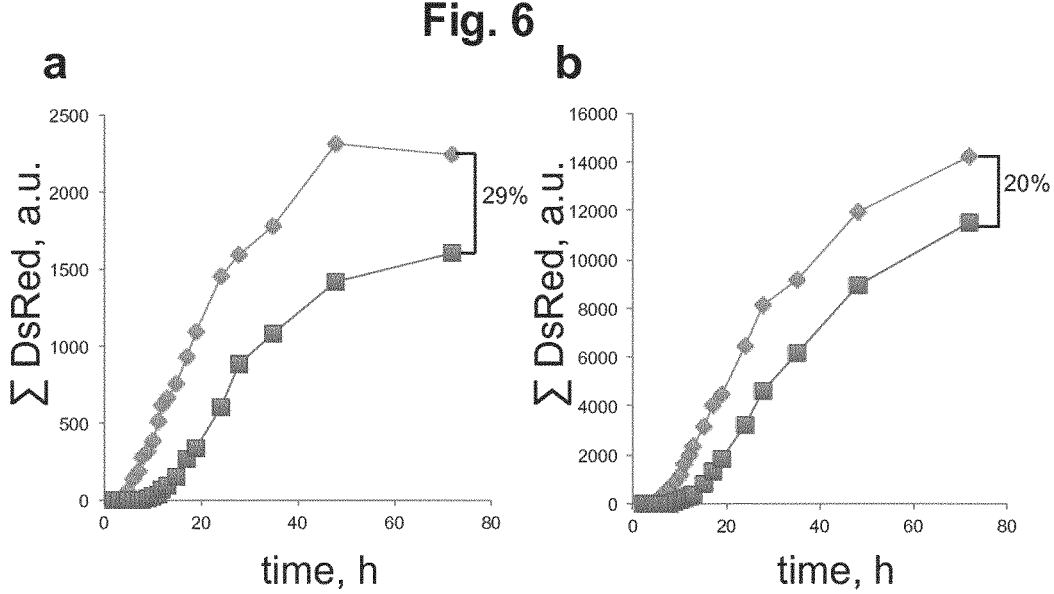
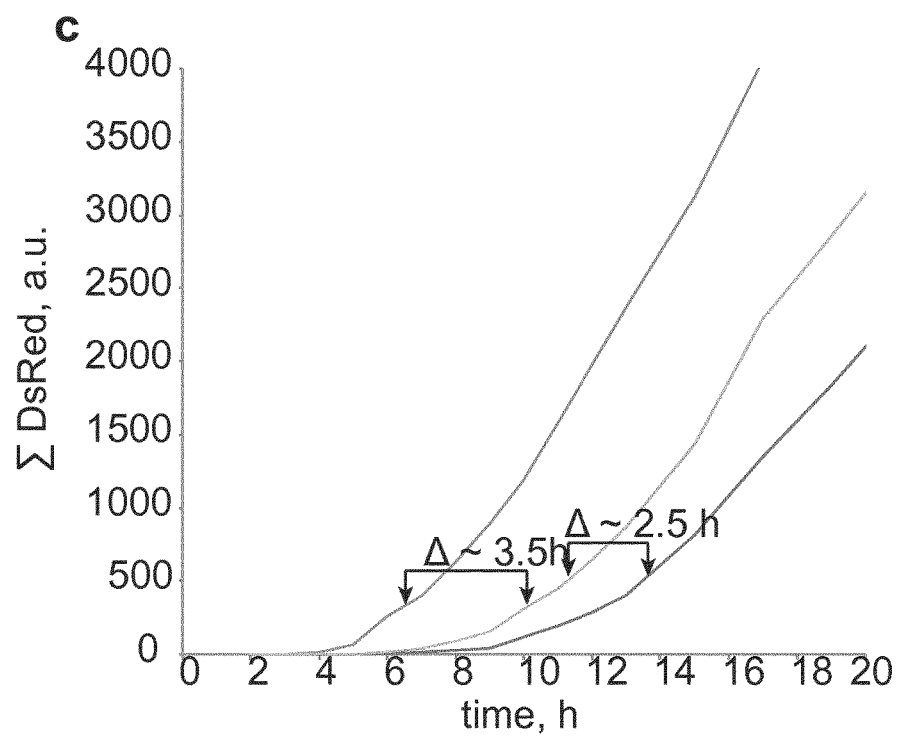
Fig. 6

Fig. 08
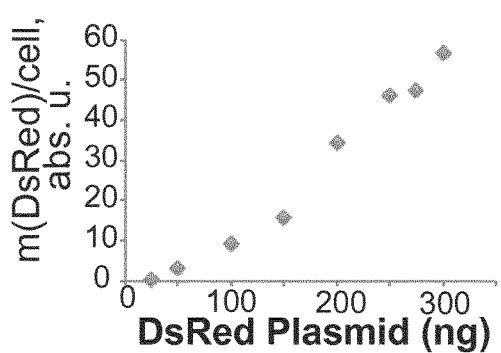
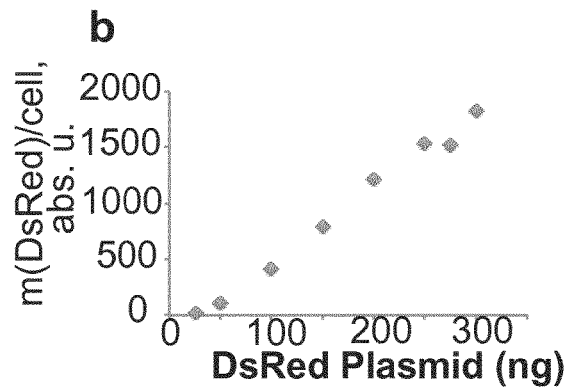
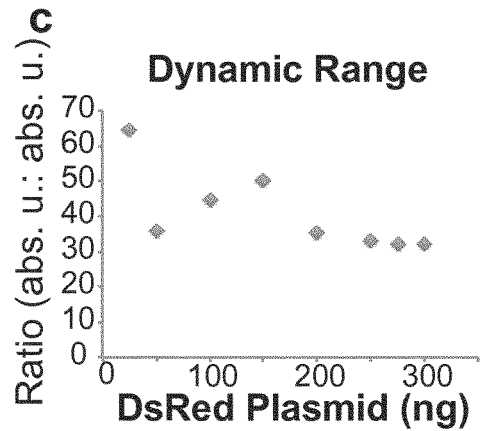
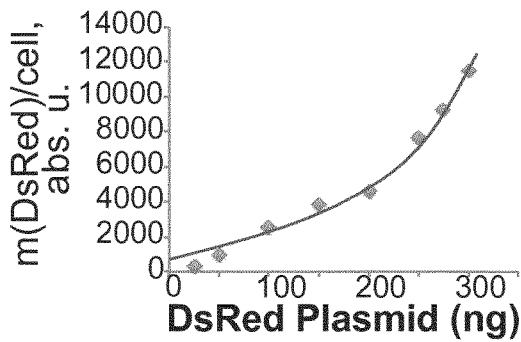
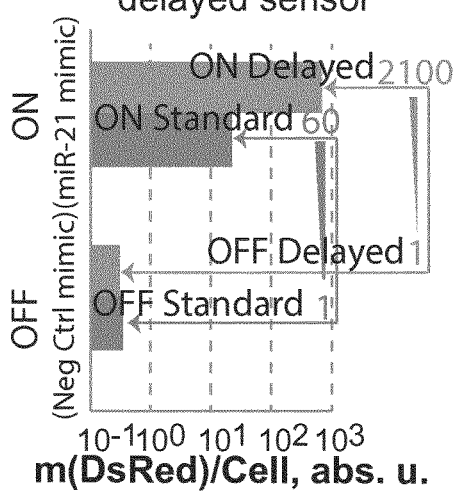
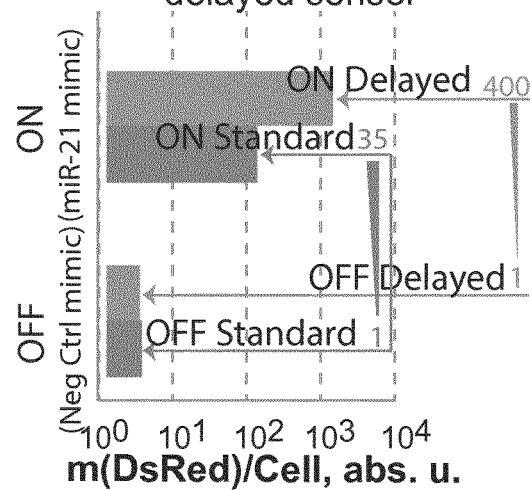

Fig. 11
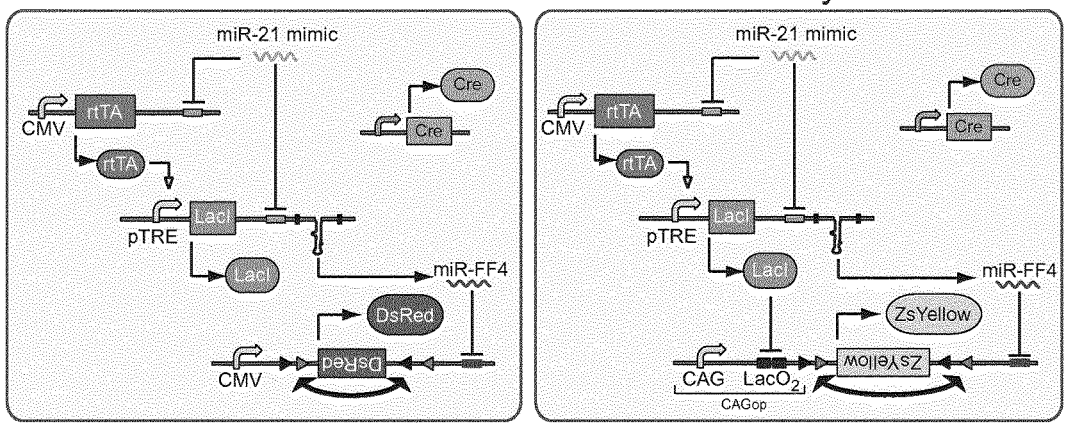
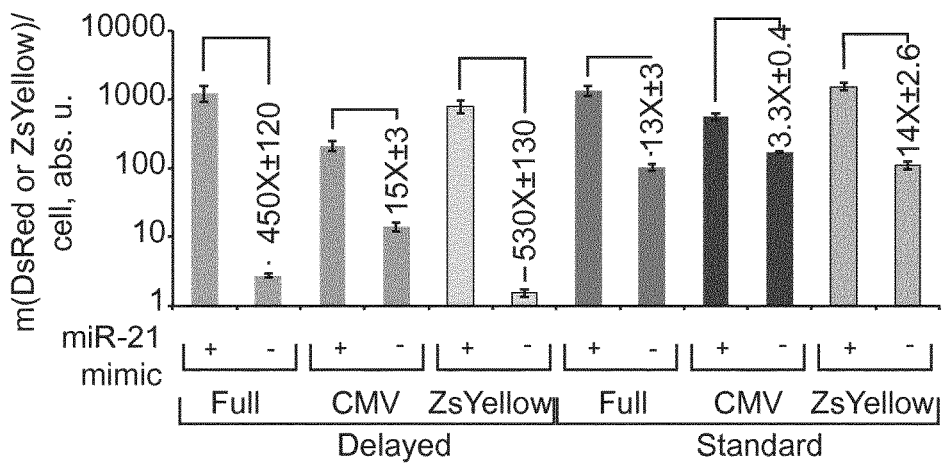

SEQUENCE LISTING

<160> NUMBER OF SEQ ID NOS: 15

<210> SEQ ID NO 1
<211> LENGTH: 34
<212> TYPE: DNA
<213> ORGANISM: Artificial Sequence
<220> FEATURE:
<223> OTHER INFORMATION: Amplification primer PR1

<400> SEQUENCE: 1
actgtgacgg taccatggcc tcctccgagg acgt                                    34

<210> SEQ ID NO 2
<211> LENGTH: 36
<212> TYPE: DNA
<213> ORGANISM: Artificial Sequence

```
<220> FEATURE:
<223> OTHER INFORMATION: Amplification primer PR2

<400> SEQUENCE: 2
actgtgacct cgagctacag gaacaggtgg tggcgg                           36

<210> SEQ ID NO 3
<211> LENGTH: 35
<212> TYPE: DNA
<213> ORGANISM: Artificial Sequence
<220> FEATURE:
<223> OTHER INFORMATION: Amplification primer PR3

<400> SEQUENCE: 3
actgtgacgc tagcttggca aagaattgga tcccc                            35

<210> SEQ ID NO 4
<211> LENGTH: 28
<212> TYPE: DNA
<213> ORGANISM: Artificial Sequence
<220> FEATURE:
<223> OTHER INFORMATION: Amplification primer PR4

<400> SEQUENCE: 4
tggcaatgcc ccaaccagtg ggggttgc                                    28

<210> SEQ ID NO 5
<211> LENGTH: 25
<212> TYPE: DNA
<213> ORGANISM: Artificial Sequence
<220> FEATURE:
<223> OTHER INFORMATION: Amplification primer PR5
<220> FEATURE:
<221> NAME/KEY: misc_structure
<222> LOCATION: (1)..(1)
<223> OTHER INFORMATION: phosphorylated

<400> SEQUENCE: 5
aaccagtaac gttatacgat gtcgc                                       25

<210> SEQ ID NO 6
<211> LENGTH: 23
<212> TYPE: DNA
<213> ORGANISM: Artificial Sequence
<220> FEATURE:
<223> OTHER INFORMATION: Amplification primer PR6
<220> FEATURE:
<221> NAME/KEY: misc_structure
<222> LOCATION: (1)..(1)
<223> OTHER INFORMATION: phosphorylated

<400> SEQUENCE: 6
catggtggga gggtacctcg cta                                         23

<210> SEQ ID NO 7
<211> LENGTH: 37
<212> TYPE: DNA
<213> ORGANISM: Artificial Sequence
<220> FEATURE:
<223> OTHER INFORMATION: Amplification primer PR7

<400> SEQUENCE: 7
ggtacttcgg cgcgccccgg tcgccaccat ggcccac                          37

<210> SEQ ID NO 8
<211> LENGTH: 36
<212> TYPE: DNA
```

<213> ORGANISM: Artificial Sequence
<220> FEATURE:
<223> OTHER INFORMATION: Amplifcation primer PR8

<400> SEQUENCE: 8
ggtacttcct cgagcggccg cttcaggcca gggcgc         36

<210> SEQ ID NO 9
<211> LENGTH: 39
<212> TYPE: DNA
<213> ORGANISM: Artificial Sequence
<220> FEATURE:
<223> OTHER INFORMATION: Amplification primer PR9

<400> SEQUENCE: 9
gccacgggcg cgccgctaga gctcgcggtg ccgaattct      39

<210> SEQ ID NO 10
<211> LENGTH: 29
<212> TYPE: DNA
<213> ORGANISM: Artificial Sequence
<220> FEATURE:
<223> OTHER INFORMATION: Amplification primer PR10

<400> SEQUENCE: 10
ggagcaggta ccgtcgactg cagaattcg                 29

<210> SEQ ID NO 11
<211> LENGTH: 35
<212> TYPE: DNA
<213> ORGANISM: Artificial Sequence
<220> FEATURE:
<223> OTHER INFORMATION: Amplification primer PR11

<400> SEQUENCE: 11
ggactgacaa gcttgatccg ccgccaccat ggtgc          35

<210> SEQ ID NO 12
<211> LENGTH: 41
<212> TYPE: DNA
<213> ORGANISM: Artificial Sequence
<220> FEATURE:
<223> OTHER INFORMATION: Amplification primer PR12

<400> SEQUENCE: 12
ggactgtgcc tgcagggttc agtccccatc ctcgagcagc c   41

<210> SEQ ID NO 13
<211> LENGTH: 32
<212> TYPE: DNA
<213> ORGANISM: Artificial Sequence
<220> FEATURE:
<223> OTHER INFORMATION: Amplification primer PR13

<400> SEQUENCE: 13
atatatgaat tcttaattca cagccaccat gc             32

<210> SEQ ID NO 14
<211> LENGTH: 33
<212> TYPE: DNA
<213> ORGANISM: Artificial Sequence
<220> FEATURE:
<223> OTHER INFORMATION: Amplification primer PR14

<400> SEQUENCE: 14
tatatcggcc gcgctttact tgtacagctc gtc            33

```
<210> SEQ ID NO 15
<211> LENGTH: 432
<212> TYPE: DNA
<213> ORGANISM: Artificial Sequence
<220> FEATURE:
<223> OTHER INFORMATION: mutant sequence gBlock 1

<400> SEQUENCE: 15
caagatagca gggaagtcaa gcttgaggtg agtatgtgct cgcttcggca gcacatatac      60
tatgttgaat gaggcttcag tactttacag aatcgttgcc tgcacatctt ggaaacactt     120
gctgggatta cttcttcagg ttaacccaac agaaggctcg agtgctgttg acagtgagcg     180
cgcagttata atataagtag atctagtgaa gccacagatg tagatctact tatgttataa     240
ctgcggtgcc tactgcctcg gagaattcaa ggggctactt taggagcaat tatcttgttt     300
actaaaactg aataccttgc tatctctttg atacatttt acaaagctga attaaaatgg      360
tataaattaa atcacttttt tcaattgttt ccttttttt cctcaggggt cgacgttgac      420
tacagccaag gt                                                         432
```

LOW-LEAKAGE CELLULAR BIOSENSOR SYSTEM

RELATED APPLICATION

This application is a National Stage of PCT/EP2015/062507, filed: Jun. 4, 2015 titled: "LOW-LEAKAGE CELLULAR BIOSENSOR SYSTEM", which claims the benefit and priority to European Application No. 14001960.5, filed on Jun. 5, 2014, all of which are incorporated by reference in their entirety for all purposes.

INCORPORATION BY REFERENCE PARAGRAPH

In compliance with 37 C.F.R. § 1.52(e)(5), the sequence information contained in electronic file name 1514261_109US9_Sequence_Listing_ST25.txt; size 3.84 KB; created on: 5 Dec. 2016; using Patent-In 3.5, and Checker 4.4.0 is hereby incorporated herein by reference in its entirety.

The present invention is directed to a cellular biosensor system comprising (A) a repressor module comprising one or more genes, which in their cumulative gene action exert repressing and/or inhibitory effect(s) on (B), an output module comprising at least one gene comprising at least one output sequence generating one or more output signals (i) in the absence of repressing and/or inhibitory effect(s) of the repressor module (A) and (ii) in the presence of at least one recombinase by (C), a recombinase module comprising at least one gene comprising at least one sequence encoding a site-specific recombinase that enables gene rearrangement in the output module resulting in one or more output signals in the absence of repressing and/or inhibitory effect(s) of the repressor module, wherein the repressing and/or inhibitory effects of the repressor module are controlled by one or more inputs that negatively affect the repressing and/or inhibitory effects of the repressor module (A). In addition, the present invention relates to a biosensor network comprising the cellular biosensor system of the present invention and their uses in the diagnosis of a disease, for drug discovery, for bio-manufacturing methods, for producing a transgenic animal, and for methods for the identification or classification of a cell status.

BACKGROUND OF THE INVENTION

Biosensing of endogenous molecular signals is used in basic research (see Siegert et al., Nature Neuroscience 2012, 15, 487-U191 and Mansfield et al., Nature Genet. 2004, 36, 1079-1083), bioproduction (see Zhang et al., Nat. Biotechnol. 2012, 30, 354-U166) and medicine (see Weber et al., Proc. Natl. Acad. Sci. USA 2008, 105, 9994-9998 and Callura et al., Proc. Natl. Acad. Sci. USA 2010, 107, 15898-15903). Proportional sensing of repressor signals is implemented by synthetic (see Gardner et al., Nature 2000, 403, 339-342; Elowitz et al., Nature 2000, 403, 335-338; Greber et al., Journal of Biotechnology 2007, 130, 329-345 and Mukherji et al., Nature Reviews Genetics 2009, 10, 859-871) "double inversion" modules that repress sensor output in the absence of input signal (Off state) and relieve repression by high input (On state) (see Rinaudo et al., Nat. Biotechnol. 2007, 25, 795-801; Deans et al., Cell 2007, 130, 363-372; Xie et al., Science 2011, 333, 1307-1311 and Haynes et al., Acs Synthetic Biology 2012, 1, 99-106). High dynamic range with such sensors has only been achieved by exogenous ligand IPTG (see Deans et al., Cell 2007, 130, 363-372), but for endogenous microRNA inputs the range has been modest.

The previously reported double inversion module (FIGS. 1a and 1b) features a gene encoding constitutively expressed rtTA activator and an rtTA-controlled gene encoding a LacI repressor and an intronic, engineered miRNA miR-FF4 (see Xie et al., Science 2011, 333, 1307-1311). LacI and miR-FF4 target the output gene transcriptionally and post-transcriptionally, respectively. Both rtTA and LacI transcripts contain tandem repeats of perfectly complementary targets of a miRNA input of interest. Thus in the absence of a miRNA input, rtTA is highly expressed inducing both LacI and miR-FF4; those in turn repress the output. When miRNA input of interest is highly expressed, rtTA, LacI and miR-FF4 levels go down, relieving repression from the output gene and generating a strong signal.

One of the main intended uses of such sensors is in diagnostic and medical applications where the genes encoding the sensors are to be delivered transiently, either using physico-chemical methods or non-integrating viral vectors (see Weber et al., Proc. Natl. Acad. Sci. USA 2010, 105, 9994-9998). In either case, not only the input may differ from cell to cell or vary over time in the same cell, but the circuit composition itself will exist most of the time outside of the steady state. First, the levels of RNA and protein components will rise; next they will remain in a quasi steady state, and finally decrease due to cell division and synthetic gene degradation.

Previously, sensor leakiness in the Off state was observed, even when the overall dynamic range (On:Off) was high. Leakiness in the Off state, regardless of the dynamic range, presents a major drawback in applications. In particular, downstream processes can be highly sensitive to low and transient amounts of output.

Recombinases have been used to control gene expression in genetic engineering applications (see Backman et al., Biotechnology 1984, 2, 10454049 and Dale et al., Proc. Natl. Acad. Sci USA 1991, 88, 10558-10562) and more recently, in biological computing circuits (see Benenson et al., Nature Reviews Genetics 2012, 13, 455-468) to implement state machines (see Ham et al., PLoS One 2008, 3), counters (see Friedland et al., Science 2009, 324, 1199-1202) and sequential logic (see Siuti et al., Nat. Biotechnol. 2013, 31, 448 and Bonnet et al., Science 2013, 340, 599-603).

The problem underlying the present invention is to improve cellular biosensor systems, in particular to minimize the leakage of a biosensor system in the non-activated state, i.e. prior to the commencement of output expression.

This object is solved in a first aspect by a cellular biosensor system comprising
(A) a repressor module comprising one or more genes, which in their cumulative gene action exert repressing and/or inhibitory effect(s) on
(B) an output module comprising at least one gene comprising at least one output sequence generating one or more output signals (i) in the absence of repressing and/or inhibitory effect(s) of the repressor module (A) and (ii) in the presence of at least one recombinase expressed by
(C) a recombinase module comprising at least one gene comprising at least one sequence encoding a site-specific recombinase that enables gene rearrangement in the output module resulting in one or more output signals in the absence of repressing and/or inhibitory effect(s) of the repressor module, wherein the repressing and/or inhibitory effects of the repressor module are controlled by one or more inputs that negatively affect the repressing and/or inhibitory effects of the repressor module (A).

The cellular biosensor system of the present invention is based on the interaction of a repressor module that is controlled by one or more inputs, preferably endogenous cellular or extracellular inputs, e.g. miRNA, proteins, antibiotics, metabolites, etc. that negatively affect the repressing and/or inhibitory effects of the repressor module (A). In other words, the repressor module functions as a sensor for the presence or absence of one or more inputs.

Next to the repressing and/or inhibitory effects of the repressor module (A) on the output module (B), e.g. by repressing a promoter and/or inhibiting expression of gene(s) of the output module, it is a preferred embodiment of the present invention that the repressor module additionally exerts repressing and/or inhibitory effects on the at least one recombinase module.

The inputs for the cellular biosensor system of the present invention are preferably selected from the group consisting of chemical compounds, metabolites, DNA, microRNA, mRNA, proteins and combinations thereof, preferably microRNA. More preferably, the inputs are selected from an inhibitor or repressor of gene expression or gene product activity, preferably a compound selected from the group consisting of endogenously expressed microRNA molecules, artificially expressed microRNA molecules, a combination of endogenously expressed and artificially expressed microRNA molecules, an antibiotic that interferes with transcription factor binding, a chemical inhibitor, a chemical interacting with a riboswitch, a small non-coding RNA, and a (poly)peptide.

In another preferred embodiment, it is preferred that the activity of at least one of modules (A), (B) and (C) is controlled by extracellular compounds, intracellular compounds or together by extracellular compounds and intracellular compounds.

Preferably, the output signal for the cellular biosensor system of the present invention is selected from the group consisting of mRNA, non-coding RNA, microRNA and (poly)peptides, preferably fluorescent proteins, more preferably green fluorescent protein (GFP), mCherry and DsRed, cell surface proteins, toxic proteins, apoptotic proteins, transcriptional regulators, immune-modulators and site-specific recombinases.

In a preferred embodiment, at least one of the genes in at least one of modules (A), (B) and (C) is replaced or supplemented with RNA or protein products to produce a functional cellular biosensor system of the present invention.

It is noted that the recombinase module (C)—expressing the site-specific recombinase that enables gene rearrangement in the output module (B) resulting in one or more output signals-does not need to be recombinantly introduced into the cellular biosensor of the present invention. The site-specific recombinase of module (C) can be naturally present in the biosensor cell. In a preferred embodiment output module (B) is designed to be responsive to and output sequence-activating in the presence of a site-specific recombinase, that is naturally expressed in the cell used for producing the biosensor of the present invention. However, it is more preferred that the recombinase module is recombinantly introduced into the biosensor cell of the present invention.

The cellular biosensor system of the present invention has the advantage that the output signal requires input-related repressor module activity in combination with recombination module (C)-expressed enzymatic recombinase activity to result in an integrated output signal. The double requirement of repressor and recombinase action for output signals minimizes signal leakage significantly. Furthermore, the preferred embodiment of regulation of the repressor module and regulation of the recombinase by identical and/or different inputs provides for a highly integrated output signal.

In the following a preferred cellular biosensor system of the present invention featuring an integrated repressor module consisting of at least two functionally interacting parts, at least one output module and at least one recombinase module is described.

In a preferred embodiment a cellular biosensor system of the invention comprises at least one gene (1) (REPRESSOR MODULE IA) comprising
   1.1 a promoter sequence (P1),
   1.2 a transcriptional activator sequence (TA) operably linked to promoter sequence (P1),
   1.3 at least one target site (T1) for one or more inputs (IN), wherein upon input (IN) binding, target site (T1) controls the expression of the transcriptional activator sequence (TA) operably linked to promoter sequence (P1);
at least one gene (2) (REPRESSOR MODULE IB) comprising
   2.1 at least one target site (T2) for one or more inputs (IN), and
   2.2 a promoter (P2) inducible by the activator expressed by transcriptional activator sequence (TA) and operably linked to either,
     (i) a transcriptional repressor sequence (TR); and/or
     (ii) one or more repressor sequences encoding at least one repressor microRNA (R-miRNA),
   wherein upon input (IN) binding, target site (T2) controls the expression of (a) the transcriptional repressor sequence (TR) and/or of (b) the at least one repressor microRNA (R-miRNA), and wherein the expressed transcriptional repressor (TR) and/or the at least one repressor microRNA (R-miRNA) control the expression of at least one output sequence;
at least one gene (3) (OUTPUT MODULE) comprising
   3.1 a promoter sequence (P3) that is repressible by the product expressed by transcriptional repressor sequence (TR) of gene (2), if gene (2) comprises the transcriptional repressor sequence (TR),
   3.2 at least one output sequence,
   3.3 at least one sequence(s) enabling gene rearrangement (SEGR) in the presence of at least one site-specific recombinase (Rec1),
   3.4 at least one target site (TmiRNA) for the at least one repressor microRNA (R-miRNA), if gene (2) comprises one or more repressor sequences encoding at least one repressor microRNA (R-miRNA),
   wherein upon gene rearrangement in the presence of at least one site-specific recombinase (Rec1), promoter (P3) is operably linked to the output sequence 3.2; and
at least one gene (4) (RECOMBINASE MODULE) comprising
   4.1 at least one promoter (P4),
   4.2 a sequence encoding the site-specific recombinase (Rec1) that enables gene rearrangement in gene (3) and operably linked to promoter (P4),
   4.3 at least one target site (T3) for one or more inputs, and
   4.4 at least one target site (TmiRNA) for the at least one repressor microRNA (RmiRNA), if gene (2) comprises one or more repressor sequences encoding at least one repressor microRNA (RmiRNA).

The principle behind the above cellular biosensor of the present invention is that endogenous and/or exogenous input signals control the expression of an output signal/OUTPUT MODULE (gene (3)) by means of functionally coupled REPRESSOR MODULES, i.e. activator (gene (1), REPRESSOR MODULE I)- and repressor (gene (2) REPRESSOR MODULE II)-controls in combination with a recombinase-mediated control (gene (4)) that significantly reduces or fully inhibits expression of the output signal in the absence of the endogenous or exogenous input signals.

In order to further prevent signal leakage of the biosensor system of the present invention the expression of the recombinase enzyme (Rec1) in gene (4) can be further controlled and, thus delayed in a preferred embodiment, wherein gene (4) requires gene rearrangement in the presence of at least one further site-specific recombinase (Rec2) to operably link promoter (P4) to the coding sequence of the site-specific recombinase (Rec1) that enables gene rearrangement of the DNA sequence(s) (SEGR).

The cellular biosensor system can operate in any suitable cell, preferably a eukaryotic cell, more preferably in a vertebrate, a mammalian, an insect, a worm or a yeast cell. In a preferred embodiment, the cellular biosensor system of the invention is one that operates in a eukaryotic cell, preferably a mammalian cell, more preferably in a human cell, most preferably in a tissue-specific mammalian cell.

The target sites for the input (IN) signals in genes (1), (2) and (4) can vary but are preferably identical so that the same one or more input signal(s) controls transcription of at least two, preferably all three genes (1), (2) and (4) at the same time, thus integrating the input signal's effect over the whole biosensor system and effectively reducing signal leakage. In a preferred embodiment of the cellular biosensor system of the present invention at least two, preferably all of the at least one target site for one or more inputs in gene (1) (T1), the at least one target site for one or more inputs in gene (2) (T2), and the at least one target site for one or more inputs in gene (4) (T3) are identical.

Gene (2) of the present invention has three structural options for controlling the output signal of gene (3). Gene (2) can feature promoter (P2) operably linked to the transcriptional repressor sequence (TR) together with at least one target site (T2) for one or more inputs (IN), and upon input (IN) binding, target site (T2) controls the expression of the transcriptional repressor sequence (TR), the expression product of which in turn represses the promoter (P3) of output gene (3). Alternatively, gene (2) can feature promoter (P2) operably linked to one or more repressor sequences encoding at least one repressor microRNA (R-miRNA), wherein the at least one repressor microRNA (R-miRNA) controls the output of the at least one output sequence of gene (3). Next to being alternatives, gene (2) can feature promoter P2 operably linked to both, the at least one target site (T2) for one or more inputs (IN), and also operably linked to the one or more repressor sequences encoding at least one repressor microRNA (R-miRNA). In this preferred embodiment, both the expressed repressor protein and the repressor microRNA (R-miRNA) control the output signal of gene (3) together.

In a preferred embodiment of the present invention, the one or more repressor sequences encoding at least one repressor microRNA (R-miRNA) in gene (2) is intronic and preferably requires splicing for encoding functional repressor microRNA (R-miRNA).

A promoter sequence is any DNA sequence that facilitates, i.e. promotes RNA transcription, and promoter activity is typically constitutive or inducible. The promoter sequence (P1) of gene (1) can be any constitutive or inducible promoter capable of facilitating RNA transcription of the transcriptional activator sequence (TA) in gene (1). In a preferred embodiment, the promoter sequence (P1) of gene (1) is selected from the group consisting of a eukaryotic cell promoter, a mammalian cell promoter, a tissue-specific promoter, an inducible artificial promoter, and an engineered constitutive promoter. The terms artificial and engineered in the context of the present invention indicate non-naturally occurring and recombinantly introduced promoters. Preferably, promoter A of gene (1) is mammalian cell promoter Elongation factor 1 alpha (EF1a) or the promoter from cytomegalovirus (CMV), a CAG, SV40 or Ubiquitin C (UBC) promoter.

The transcriptional activator sequence (TA) of gene (1) is operably linked to promoter sequence P1 and encodes a (poly)peptide sequence capable of activating transcription from a suitable inducible promoter. In a preferred embodiment, the transcriptional activator sequence of gene (1) encodes artificial eukaryotic transactivators, preferably tetracycline-dependent transcriptional activator (tTA or rtTA), or natural eukaryotic activators, preferably Sp1. Activators from other species can be adapted to eukaryotic cells in which the biosensor of the present invention preferably operates (see Hansen et al., Proc. Natl. Acad. Sci USA 2014, 111, 15705-10 and Stanton et al., ACS Synth. Biol., 2014, 3, 880-91.).

The at least one target sites (T1, T2 and T3) for one or more inputs of genes (1), (2) and (4) are any sequence that is targeted by the at least one or more inputs (IN), and upon input binding the target sites (T1, T2, T3) control the expression of the nucleotide sequences (TA) of genes (1), (2) and (4).

The term "one or more inputs for a target site" as defined herein for genes (1), (2) and (4) means a compound binding specifically to a target site and preferably functioning as any inhibitor or repressor of gene expression or gene product activity in said gene. In a preferred embodiment the one or more inputs for use in the present invention are selected from the group consisting of endogenously expressed microRNA molecules, artificially expressed microRNA molecules, a combination of endogenously expressed and artificially expressed microRNA molecules, an antibiotic that interferes with transcription factor binding, a chemical inhibitor, a chemical interacting with a riboswitch, a small non-coding RNA, and a (poly)peptide. Endogenously expressed refers to compounds naturally produced by the cell encompassing the biosensor system of the present invention, whereas artificially expressed refers to compounds produced by the cell upon artificial manipulation, e.g. recombinant modification.

In a preferred embodiment, the input compound is a nucleotide sequence, preferably a microRNA, and at least one of the target site sequence is fully or partially complementary to the input nucleotide sequence. Preferably, the target sites (T1, T2, T3) in genes (1), (2) and (4) comprise a number of identical repeats that fully or partially complementary to the input nucleotide sequence, more preferably 1 to 20 repeats.

In a further preferred embodiment, at least one of the one or more inputs for at least one target site (T1, T2, T3) in genes (1), (2) and (4) is a non-micro RNA input interacting with the target site, preferably the target site sequence is a riboswitch that can be inhibited by a small molecule-, an RNA- or a protein-input.

In a more preferred embodiment, the at least one target site (T1, T2, T3) in genes (1), (2) and (4) is embedded in the 3'-untranslated region or the 5'-untranslated region of these genes, or overlaps with the coding sequence of activator (TA) of gene (1), or overlaps with the transcriptional repressor sequence (TR) of gene (2).

It is noted that the one or more inputs for the at least one target site (T1, T2, T3) in genes (1), (2) and (3) preferably interact with the genes on the post-transcriptional, i.e. mRNA level.

Gene (2) comprises a promoter (P2) inducible by the activator expressed by transcriptional activator sequence (TA) in gene (1). Induction of promoter P2 by the activator expressed by gene (1) may require the presence of a chemical compound-, an RNA- or a protein-cofactor. In a preferred embodiment, the inducible promoter is a pTRE promoter or any promoter inducible by transactivator(s).

The transcriptional repressor sequence (TR) of gene (2) encodes a repressor compound capable of repressing transcription from a suitable repressible promoter (P2). Preferably, the repressor encoded by the transcriptional repressor sequence (TR) of gene (2) is selected from the group consisting of a (poly)peptide repressor, a non-coding RNA repressor, preferably a small or long non-coding RNA repressor, a combination of different repressors, preferably a combination of a protein repressor and a non-coding RNA repressor, a combination of two repressor proteins linked via a peptide linker or peptide cleavage site (2A), and an internal ribosome entry site (IRES). The transcriptional repressor sequence (TR) of gene (2) is preferably an artificial or natural eukaryotic repressor including natural repressors from other species adapted to the biosensor cells of the present invention, more preferably, the transcriptional repressor sequence (TR) of gene (2) it is LacI or LacIKrab.

Gene (2) may optionally feature one or more transcriptional repressor sequences encoding at least one repressor microRNA (R-miRNA), wherein the at least one repressor microRNA (R-miRNA) controls the expression of at least one output sequence. The repressor sequence can be an intron embedded in the 3'-untranslated region, an intron embedded in the 5'-untranslated region, or an intron embedded in the one or more transcriptional repressor sequences (TR) encoding at least one repressor microRNA (R-miRNA). The repressor sequence can be intronic or non-intronic. The repressor microRNA (R-miRNA) can be endogenous, artificial or partially artificial to the biosensor cell of the present invention.

The promoter sequence (P3) of gene (3), also designated "output gene", can be any constitutive, inducible or repressible promoter capable of facilitating RNA transcription of the at least one output sequence in gene (3). If gene (2) comprises the transcriptional repressor sequence (TR), then gene (3) comprises a promoter sequence (P3) that is repressible by the product expressed by the transcriptional repressor sequence (TR) of gene (2). In a preferred embodiment, the promoter sequence (P3) of gene (3) is selected from the group consisting of a eukaryotic cell promoter, a mammalian cell promoter, a tissue-specific promoter, an inducible artificial promoter, and an engineered constitutive promoter, preferably Elongation factor 1 alpha (EF1a), CAGop, cytomegalovirus (CMV), SV40 or Ubiquitin C (UBC) promoters.

The output sequence of gene (3) produces an RNA product, for example, coding mRNA, non-coding mRNA, microRNA, and the RNA product is preferably further fully or partially translated into a (poly)peptide. In a preferred embodiment output products of the biosensors of the present invention are selected from the group consisting of mRNA, non-coding RNA, microRNA and (poly)peptides, preferably fluorescent proteins, more preferably green fluorescent protein (GFP) and DsRed, cell surface proteins, toxic proteins, apoptotic proteins, transcriptional regulators, immune modulators and site-specific recombinases. Preferably, the output product allows for easy detection, e.g. by optical methods such as microscopy, UV-VIS-light detection, binding assays, morphological changes of the biosensor cells, cell motility etc.

Gene (3) comprises at least one sequence(s) enabling gene rearrangement (SEGR) in the presence of at least one site-specific recombinase (Rec1) wherein upon gene rearrangement in the presence of at least one site-specific recombinase (Rec1) promoter (P3) is operably linked to the output sequence of gene (3). In the absence of the at least one site-specific recombinase (Rec1) gene (3) is incapable to produce RNA and/or proteins from the output sequence.

Gene (3) also comprises at least one rearrangement sequence(s) enabling gene rearrangement (SEGR) in the presence of at least one site-specific recombinase (Rec1). The rearrangement sequence(s) (SEGR) controls the orientation and/or specific genetic sequence of at least one of the promoter P3 and the at least one output sequence in the presence of at least one site-specific recombinase (Rec1).

The configuration, i.e. location and sequences of the rearrangement sequence(s) (SEGR) can vary between implementations. Preferably, every such configuration confers either lack of expression of the at least one output sequence, or expression of a non-functional version of the at least one output sequence in the absence of a site-specific recombinase that is operably, i.e. functionally linked to the rearrangement sequence(s) (SEGR). In the presence of a site-specific recombinase (Rec1) the rearrangement sequence(s) (SEGR) guide the genetic rearrangement to result in the expression of functional outputs. In a preferred embodiment, the at least one sequence(s) enabling gene rearrangement (SEGR) is the FLeX switch that is based on (i) LoxP sites and Cre recombinase or on other Cre recombinases with improved accuracy (Eroshenko, Nat. Commun. 2013, 4:2509), or based on (ii) FRT sites and Flp recombinase, or any recombinase from the serine and the tyrosine family, or any fusion protein with recombinase activity, preferably estrogen receptor fused to Cre (e.g. ER-iCre or ER-iCRE-ER) (for a review see Atasoy et al., J. Neurosci. 2008, 28, 7025-7030 or Grindely et al., Annu. Rev. Biochem. 2006, 75,567-605).

If gene (2) comprises one or more repressor sequences encoding at least one repressor microRNA (R-miRNA), the at least one target site (TmiRNA) in gene (3) for the at least one repressor microRNA (R-miRNA) of gene (2) is preferably embedded in the 3'-untranslated region of gene (3), the 5'-untranslated region of gene (3), or overlaps with the at least one output sequence of gene (3). The at least one target site (TmiRNA) in gene (3) is fully or partially complementary to the at least one repressor microRNA (R-miRNA) of gene (2) and preferably comprises identical repeats, more preferably 1 to 20 repeats.

The promoter sequence (P4) of gene (4), also designated "recombinase gene", can be any constitutive or inducible promoter capable of facilitating RNA transcription of the sequence encoding of the site-specific recombinase (Rec1) that enables gene rearrangement in gene (3). In short, promoter (P4) of gene (4) is operably linked to the sequence encoding the site-specific recombinase (Rec1). In a preferred embodiment, the promoter sequence (P4) of gene (4) is selected from the group consisting of a eukaryotic cell promoter, a mammalian cell promoter, a tissue-specific promoter, an inducible artificial promoter, and an engineered constitutive promoter, preferably the group consisting of Elongation factor 1 alpha (EF1a), CAGop, cytomegalovirus (CMV), SV40 and Ubiquitin C (UBC) promoters, TRE promoter, erythromycin inducible promoter (ETR, see Weber et al., Nat Biotechnol. 2002, 20, 901-7), and pristinamycin inducible promoter (PIR, see Weber et al., Nat Biotechnol. 2002, 20, 901-7).

In a most preferred embodiment, the sequence encoding the site-specific recombinase (Rec1) in gene (4) is preferably derived from phages, bacteria, yeast, etc. and is adapted to the biosensor cell of the present invention, preferably a eukaryotic biosensor cell. The site-specific recombinase (Rec1) in gene (4) can be an engineered or modified site-specific recombinase, preferably selected from the group consisting of Cre, Flp and PhiC31, or any recombinase from the serine or tyrosine family or any fusion protein with recombinase activity, preferably estrogen receptor fused to Cre (e.g. ER-iCre or ER-iCRE-ER), and the recombinase may optionally require a cofactor such as a chemical compound, preferably Tamoxifen, an RNA or a protein to trigger the genetic rearrangement in gene (3).

If gene (2) comprises one or more repressor sequences encoding at least one repressor microRNA (R-miRNA), the at least one target site (TmiRNA) in gene (4) for the at least one repressor microRNA (R-miRNA) of gene (2) is embedded in the 3'-untranslated region of gene (4), the 5'-untranslated region of gene (4), or overlaps with the sequence encoding the site-specific recombinase (Rec1) enabling gene rearrangement in gene (3). The at least one target site (TmiRNA) in gene (4) is fully or partially complementary to the at least one repressor microRNA (R-miRNA) of gene (2) and preferably comprises identical repeats, more preferably 1 to 20 repeats.

In a more specific embodiment, gene (4) may also comprise at least one rearrangement sequence(s) enabling gene rearrangement (SEGR) in the presence of at least one further site-specific recombinase (Rec2). The optional rearrangement sequence(s) (SEGR) in gene (4) controls the orientation and/or specific genetic sequence of at least one of the promoter P4 and the sequence encoding the site-specific recombinase (Rec1) enabling gene rearrangement in gene (3). In other words, the further recombinase (Rec2) controls the rearrangement in gene (4) leading to the recombinase (Rec1) that controls the rearrangement in gene (3), thus producing the output product.

In a preferred embodiment, the cellular biosensor system of the present invention further comprises a gene (5) encoding the further recombinase (Rec2) that controls genetic rearrangement in gene (4).

In the following, most preferred embodiments of the cellular biosensor system of the present invention are described.

A cellular biosensor system of the present invention, wherein gene (1) comprises (see CMV-rtTA-T21 plasmid DNA construct in the examples)
   1.1 a CMV promoter for promoter sequence (P1),
   1.2 an rtTA transactivator encoding sequence for transcriptional activator sequence (TA),
   1.3 four repeats of T21 for target site (T1),
   wherein upon input (miR-21) binding, target sites (4×T21) control the expression of the transcriptional activator sequence (rtTA) operably linked to promoter sequence (CMV);
gene (2) comprises (see TRE-LacI-T21-miR-FF4 plasmid DNA construct in the examples)
   2.1 a TRE promoter for promoter (P2) inducible by the activator expressed by the transcriptional activator sequence (rtTA),
   2.2 a LacI repressor encoding sequence operably linked to the promoter for transcriptional repressor sequence (TR), with 4 target sites for miR-21 and one synthetic microRNA (miR-FF4) spliced in the 3'UTR of the gene for sequences encoding a repressor microRNA, wherein upon input (miR-21) binding, the target sites (4×T21) control the expression of the transcriptional repressor sequence (LacI) operably linked to promoter sequence TRE, and wherein the repressor microRNA (R-miRNA) controls the expression of the output sequence;
gene (3) comprises (see CAGop-Lox2272-LoxP-Reverse-DsRed-Lox2272-LoxP-FF4 plasmid DNA construct in the example section)
   3.1 a CAGop promoter for promoter sequence (P3) that is repressible by the product expressed by the transcriptional repressor sequence (LacI) of gene (2),
   3.2 a DsRed encoding sequence in reverse orientation for output sequence,
   3.3 4 recombination sequences (2× Lox2272 and 2× LoxP as described in Schnutgen et al., Nat. Biotechnol. 2003, 21, 562-565) for gene rearrangement (SEGR) in the presence of the site-specific recombinase (iCre),
   3.4 4 repeats of an miR-FF4 target site (4×TFF4) for the repressor microRNA (R-miRNA); and
gene (4) comprises (see SV40-iCre plasmid DNA construct in the example section)
   4.1 an SV40 promoter for promoter (P4),
   4.2 an iCre encoding sequence for sequence encoding the site-specific recombinase (Rec1) that enables gene rearrangement in gene (3) and operably linked to the promoter (SV40).

A cellular biosensor system of the present invention, wherein
gene (1) comprises (see CMV-rtTA-T21 plasmid DNA construct in the examples section)
   1.1 a CMV promoter for promoter sequence (P1),
   1.2 an rtTA transactivator encoding sequence for transcriptional activator sequence (TA) operably linked to the promoter sequence (P1),
   1.3 4 repeats of T21 for target site (T1),
   wherein upon input (miR-21) binding, the target sites (4×T21) control the expression of the transcriptional activator sequence (rtTA) operably linked to the promoter sequence (CMV);
gene (2) comprises (see TRE-LacI-T21-miR-FF4 plasmid DNA construct in the examples section)
   2.1 a TRE promoter for promoter (P2) inducible by the activator expressed by the transcriptional activator sequence (rtTA),
   2.2 a LacI repressor encoding sequence operably linked to the promoter for transcriptional repressor sequence (TR), with 4 target sites for miR-21 and one synthetic microRNA (miR-FF4) spliced in the 3'UTR of the gene for sequences encoding a repressor microRNA, wherein upon input (miR-21) binding, the target sites (4×T21) control the expression of the transcriptional repressor sequence (LacI) operably linked to promoter sequence TRE, and wherein the repressor microRNA (R-miRNA) controls the expression of the output sequence;
gene (3) comprises (see CAGop-Lox2272-LoxP-Reverse-DsRed-Lox2272-LoxP-FF4 plasmid DNA construct in the examples section)
   3.1 a CAGop promoter for promoter sequence (P3) that is repressible by the product expressed by the transcriptional repressor sequence (LacI) of gene (2), 3.2 a DsRed encoding sequence in reverse orientation for output sequence, 3.3 4 recombination sequences (2× Lox2272 and 2× LoxP as described in Schnutgen et al., Nat. Biotechnol. 2003, 21, 562-565) for gene rearrangement (SEGR) in the presence of the site-specific recombinase (iCre), 3.4 4 repeats of a miR-FF4 target site (4×TFF4) for the repressor microRNA (R-miRNA);

gene (4) comprises (see CMV-FRT-F3-Reverse_iCre-FRT-F3 plasmid DNA construct in the examples section)

4.1 a CMV promoter for promoter (P4), 4.2 an iCre encoding sequence in the reverse orientation for sequence encoding the site-specific recombinase (Rec1) that enables gene rearrangement in gene (3) and operably linked to the promoter (SV40), 4.3 4 recombination sequences (2×FRT and 2×F3) for gene rearrangement (SEGR) in the presence of a second site-specific recombinase (FLP); and gene 5 comprises (see EF1a-Flp construct in the examples section)

5.1 an EF1a promoter for promoter of the second recombinase (Rec2), 5.2 an Flp encoding sequence for sequence encoding the second site-specific recombinase (Rec2).

A cellular biosensor system of the present invention, wherein gene (1) comprises (see CMV-rtTA-T21 plasmid DNA construct in the examples section)

1.1 a CMV promoter for promoter sequence (P1), 1.2 an rtTA transactivator encoding sequence for transcriptional activator sequence (TA) operably linked to the promoter sequence (P1), 1.3 4 repeats of T21 for target site (T1), wherein upon input (miR-21) binding, the target sites (4×T21) control the expression of the transcriptional activator sequence (rtTA) operably linked to the promoter sequence (CMV);

gene (2) comprises (see TRE-LacI T21-miR-FF4 plasmid DNA construct in the examples section)

2.1 a TRE promoter for promoter (P2) inducible by the activator expressed by the transcriptional activator sequence (rtTA), 2.2 a LacI repressor encoding sequence operably linked to the promoter for transcriptional repressor sequence (TR), with 4 target sites for miR-21 and one synthetic microRNA (miR-FF4) spliced in the 3'UTR of the gene sequences encoding a repressor microRNA;

wherein upon input (miR-21) binding, the target sites (4×T21) control the expression of the transcriptional repressor sequence (LacI) operably linked to promoter sequence TRE, and wherein the repressor microRNA (R-miRNA) control the expression of the output sequence;

gene (3) comprises (see CAGop-Lox2272-LoxP-Reverse-DsRed-Lox2272-LoxP-FF4 plasmid DNA construct in the examples section)

3.1 a CAGop promoter for promoter sequence (P3) that is repressible by the product expressed by the transcriptional repressor sequence (LacI) of gene (2), 3.2 a DsRed encoding sequence in reverse orientation for output sequence, 3.3 4 recombination sequences (2× Lox2272 and 2× LoxP as described in Schnutgen et al., Nat. Biotechnol. 2003, 21, 562-565) for gene rearrangement (SEGR) in the presence of the site-specific recombinase (iCre), 3.4 4 repeats of an miR-FF4 target site (4×TFF4) for the repressor microRNA (R-miRNA); and gene (4) comprises (see CAG-ERT2-iCre-ERT2 plasmid DNA construct in the examples section)

4.1 a CAG promoter used for promoter (P4), 4.2 an iCre encoding sequence fused to mutant estrogen receptors (see Indra et al., Nucleic Acids Res. 1999, 27, 4324-7) for sequence encoding the site-specific recombinase (Rec1) that enables gene rearrangement in gene (3) and temporal control of iCre translocation upon addition of Tamoxifen and which is operably linked to promoter (CAG).

In a further aspect, the present invention relates to a biosensor network that comprises at least one cellular biosensor system of the present invention, preferably a cellular biosensor system as described above, comprising one or more repressor modules, one or more recombinase modules and one or more output modules, wherein at least two modules thereof respond to different inputs, preferably respond to different endogenous or synthetic microRNA inputs, all of which inputs together control the output of the one or more output modules.

The cellular biosensor system or biosensor network of the present invention can be used in the diagnosis of a disease, preferably a human disease, more preferably a disease selected from the group consisting of cancer, genetic diseases, immune disorders, infectious disease and metabolic diseases.

Alternatively, the cellular biosensor system or biosensor network of the present invention can be used for drug discovery, preferably in cell-based or in vivo assays determining drug efficacy and/or drug toxicity.

The cellular biosensor system and biosensor network of the present invention can be used for product bio-manufacturing methods, wherein the cellular and biosensor networks control the expression of a biological product of interest, preferably the expression of an antibody, an immune modulator, growth factor, serum compound, food or feed additive, polypeptide drug or a vaccine.

Moreover, the cellular biosensor system and the biosensor network of the present invention can be used for producing a transgenic animal comprising a cellular biosensor system or a biosensor network of the present invention.

In a further aspect, the present invention concerns a method for the identification or classification of a cell status, preferably a physiological or pathological cell state, a differentiation state, a cell cycle state, in a cell, a cell culture, a tissue culture or an animal comprising a cellular biosensor system or a biosensor network of the present invention.

In addition, the present invention encompasses any transgenic animal, preferably a mammal, comprising a cellular biosensor system or a biosensor network of the present invention.

Furthermore, the present invention relates to a method for producing a cellular biosensor system or a biosensor network of the invention comprising the steps of introducing a repressor module, an output module, and a recombinase module as defined above into a cell, preferably a mammalian, more preferably a human cell, to produce a cellular biosensor of the invention.

In a further aspect, the present invention relates to a cellular biosensor system as described above but without the recombinase module.

In a preferred embodiment, this cellular biosensor system comprises (A) a repressor module comprising one or more genes, which in their cumulative gene action exert repressing and/or inhibitory effect(s) on (B) an output module comprising at least one gene comprising at least one output sequence generating one or more output signals (i) in the absence of repressing and/or inhibitory effect(s) of the repressor module (A), wherein the repressing and/or inhibitory effects of the repressor module are controlled by one or more inputs that negatively affect the repressing and/or inhibitory effects of the repressor module (A).

In a more preferred embodiment the cellular biosensor system of the above aspect is one wherein the repressing and/or inhibitory effects of the repressor module (A) on the output module (B) do not include output (B) promoter-directed repression by a repressor protein expressed by repressor module (A).

In a most preferred embodiment, the cellular biosensor system of the above aspect is one wherein the repressing and/or inhibitory effects of the repressor module (A) are mediated by at least one repressor microRNA (R-miRNA) expressed by repressor module (A) and specifically binding to the output module (B) comprising at least one target site (TmiRNA) for the at least one repressor microRNA (R-miRNA).

In a more specific embodiment, the present invention is directed to a cellular biosensor system according to the above aspect comprising at least one gene (1) (REPRESSOR MODULE IA) comprising 1.1 a promoter sequence (P1),
1.2 a transcriptional activator sequence (TA) operably linked to promoter sequence (P1),
1.3 at least one target site (T1) for one or more inputs (IN), wherein upon input (IN) binding, target site (T1) controls the expression of the transcriptional activator sequence (TA) operably linked to promoter sequence (P1);

at least one gene (2) (REPRESSOR MODULE IB) comprising 2.1 at least one target site (T2) for one or more inputs (IN), or no target site (T2) for one or more inputs (IN), and
2.2 a promoter (P2) inducible by the activator expressed by transcriptional activator sequence (TA) and operably linked to one or more repressor sequences encoding at least one repressor microRNA (R-miRNA),
wherein upon input (IN) binding, target site (T2) controls the expression of the at least one repressor microRNA (R-miRNA), and wherein the at least one repressor microRNA (R-miRNA) controls the expression of at least one output sequence;

at least one gene (3) (OUTPUT MODULE) comprising 3.1 a promoter sequence (P3),
3.2 at least one output sequence,
3.3 at least one target site (TmiRNA) for the at least one repressor microRNA (R-miRNA).

Preferably, the cellular biosensor system of the invention is one wherein at least two, preferably all of the at least one target site for one or more inputs in gene (1) (T1), the at least one target site for one or more inputs in gene (2) (T2), and the at least one target site for one or more inputs in gene (3) are identical.

With regard to the above aspect of the present invention referring to a biosensor system without recombinase-dependent output module, it is noted that the definitions for and examples of components such as inputs, outputs, promoters, transcriptional activators, target sites, etc. also apply to the above aspect without recombinase output control. Furthermore, the biosensors of the present invention without recombinase-controlled output can also form part of a biosensor network, can be for diagnostic use, for drug discovery, for product biomanufacturing methods and for producing a transgenic animal, the same as described above for the cellular biosensors of the present invention that feature a recombinase module.

The above-described modules for use in all aspects of the present invention can be produced in various ways by the average skilled person in the field of genetic engineering, as generally discussed in the following and as specifically illustrated in the appended Examples, Figures and Tables.

For example, for plasmid-based encoding and transient delivery, the genes of interest can be cloned into suitable plasmids and delivered to cultured, e.g. mammalian cells, or to a whole organism using a suitable delivery method, e.g. chemical delivery methods including, but not limited, to liposomal vesicles. Each gene can be encoded on a separate plasmid, or two or more genes can be combined on the same plasmid backbone.

For example, for viral encoding and transient delivery, the genes can be embedded in suitable non-integrating viral vectors for implementation in cultured cells, e.g. mammalian cells, and in vivo, including, but not limited to, gene therapy applications in human patients. All the genes can be embedded in a single viral genome, or subsets of genes can be embedded in distinct viral genomes. In the latter case, coinfection of a cell with two or more viral vector types may be required for full sensor operation. Furthermore, the viral vectors include non-replicating viruses, replicating viruses and oncolytic viruses. Preferred examples are adenovirus, adeno-associated virus (AAV), herpes simplex virus (HSV), vaccinia virus, etc.

For example, for viral encoding and stable delivery the genes can be embedded in suitable integrating viral vectors. All the genes can be embedded in a single viral genome, or subsets of genes can be embedded in distinct viral genomes. In the latter case, coinfection of a cell with two or more viral vector types may be required for full sensor operation. Preferably, the viral vectors are retroviruses and lentiviruses. A biosensor encoded in a retroviral vector can be used in vivo in animal models, or for human therapy, for example in hematopoietic stem cell therapy or other immune disorders where stable integration is required.

For example, for non-viral stable delivery the genes can be embedded in eukaryotic cells via targeted or non-targeted genome editing and used in transgenic animal models or in cell culture.

In some cases it may be advantageous to stably implant certain genetic components while delivering others transiently in trans. Thus, all the above-described general methods can be used both separately and in combination when required by an application.

In the following the invention will be illustrated in more detail by practical examples and with reference to Figures and Tables, none of which are to be interpreted as limiting the scope of the invention beyond the claims as appended.

FIGURES

Detailed Description of the Figures

FIG. 1. Source of leakage in a proportional sensor. a) General layout of a proportional sensor for a negative regulator. An input elicits inhibitory effect on a double-inversion module, which in turn negatively regulates the output. b) Circuit diagram of the proportional microRNA sensor, as reported in Xie et al., Science 2011, 333, 1307-1311. Pointed arrows indicate activation while blunted arrows denote repression. Rectangles targeted by miRNA represent four identical sites for miR-21 and three identical sites for miR-FF4. c) Total output signal shown as a function of time in both On and Off sensor states. The signal is the sum of all DsRed intensities in DsRed-positive cells. The signal is not normalized because the expression of the transfection marker AmCyan showed very similar dynamics in all cases. Inset, full dynamics over 72 hours. d) Flow cytometry scatter plots measured at indicated times post-transfection in Off (top) and On (bottom) states. The dotted line is the upper threshold on the output level in the Off state. The charts on the left show mean fluorescence of DsRed-expressing cells in Off (top) and On (bottom) states, respectively, as a function of time. Transfection protocols for all experiments are summarized in FIGS. 5, 12 and Tables 1-3.

FIG. 2. The effect of delayed output on sensor performance. a) The principle behind the FLEx inversion system (see Schnutgen et al., Nat. Biotechnol. 2003, 21, 562-565). b-e) Time course measurements of standard and delayed sensor architectures. An equivalent of 5 ng of EF1A-iCre construct per 12-well transfection is used in all experiments for proper side-by-side comparison. Forward-facing output constructs are generated by in vitro recombination of backward-facing output gene in the presence of Cre and they contain two incompatible Lox sites. Transfection protocols for all experiments are summarized in FIGS. 5, 12 and Tables 1-3. b) Time course of total output protein expression from the uncontrolled forward-facing output gene (Standard, Top) and delayed output expression from uncontrolled backward-facing output gene (Delayed, Top), showing about a 6 h delay. In the same plot, the time course of On signal development in the standard (Standard, On) was compared to the delayed (Delayed, On) sensor and an 8 h delay was observed. Only the first 14 h are shown. c) Time course of total DsRed signal corresponding to the uncontrolled output gene (Top), miR-21 sensor in the presence of miR-21 mimic (On) and sensor in the presence of negative control mimic (Off), corresponding to both standard and delayed configurations as indicated in the chart, over 72 h. The fold-ratios between the On and the Off signals are shown. Line 1 corresponds to the Off state of the standard sensor in the absence of any miRNA mimic (also see Contents and results obtained according to the Figures below). d) Time-dependent histograms of DsRed output in the standard sensor configuration. Different set-ups are indicated on top. The label "Upper output bound" corresponds to DsRed expression from uncontrolled output gene (same as "Top" in b) and c)). e) Time course measurements in the delayed configuration. The Off and On time series are as in d). The "Upper output bound" shows the dynamics of DsRed expression from the uncontrolled backward-facing output gene in the presence of Cre (same as "Top" in b) and c)). f) Delayed sensor characterization as a function of Cre-expressing plasmid amount. The top and the bottom chart rows correspond to On and Off states, respectively. The charts in the left column show the proportion of cells expressing DsRed. The charts in the middle show total DsRed signal normalized by total AmCyan signal and thus normalized to nonspecific differences in transfection efficiency and expression strength. The right column shows DsRed signal calculated as a mean DsRed value per transfected cell, where the number of transfected cells is determined using AmCyan transfection marker. The curves are fitted to Hill function with $n=1$ (On states) and to power law (Off states). g) Measured and predicted On:Off sensor ratio (a.k.a. dynamic range) as a function of Cre amount. The curve is calculated by dividing the fitted curves of the On by the Off measurements. h) Mean DsRed levels in DsRed-positive cells in the On state.

Figure 3:
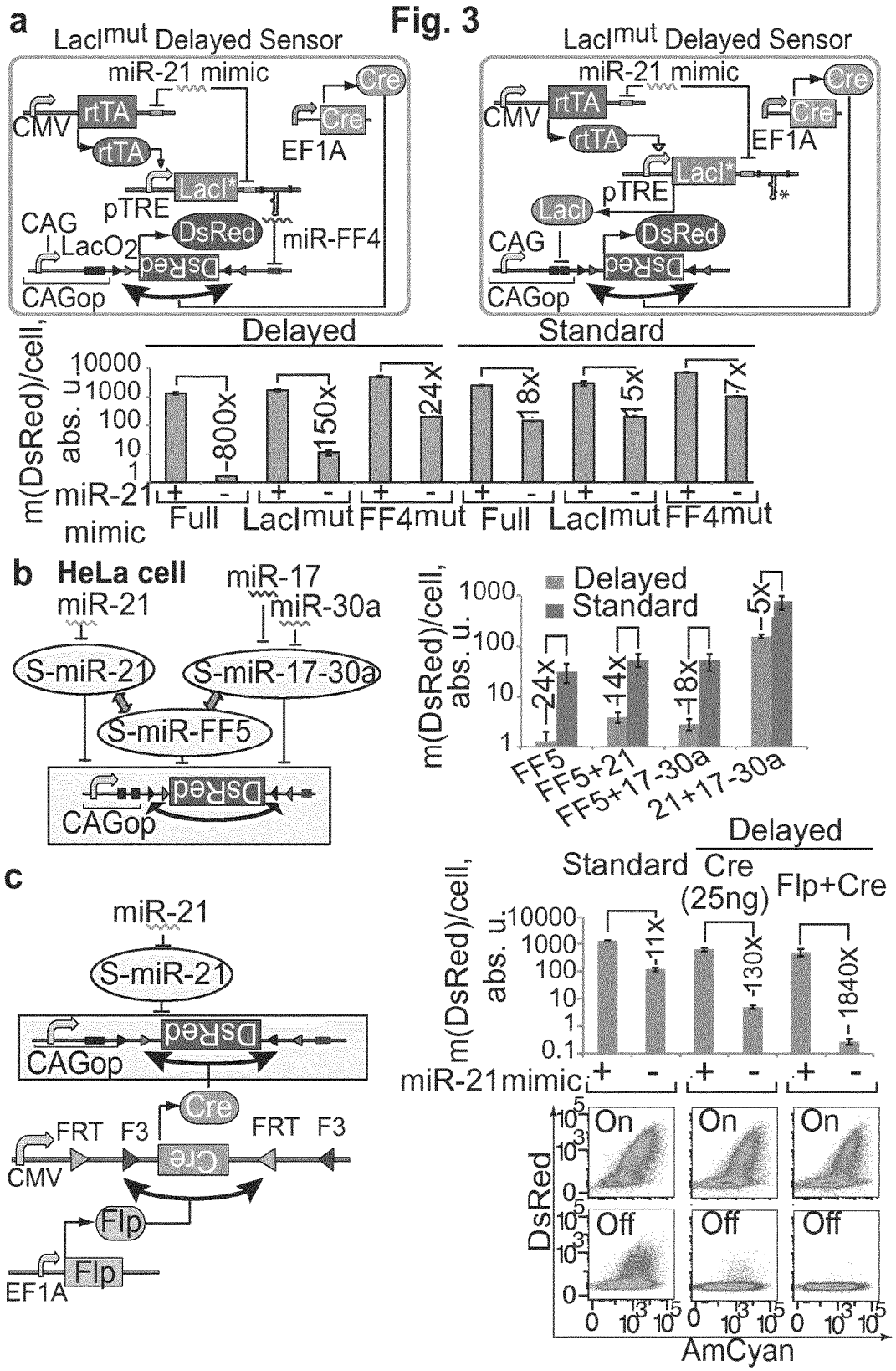

FIG. 3. In-depth sensor characterization in additional context. a) Circuit diagrams of the mutant sensor versions and their relative performance. b) Sensor incorporation in two-input AND logic gate using endogenous miR-21, miR-17 and miR-30 inputs in HeLa cells. S-miR-21 and S-miR-17-30a denote double-inversion modules of miR-21 and miR-17+miR-30a sensors, namely, the rtTA cassette and the LacI-miR-FF4 cassette with appropriate miRNA targets. S-miR-FF5 denotes a mutated module where the endogenous miRNA target is replaced with inert target sequence called FF5. This sensor does not respond to any endogenous miR and thus it emulates a logical Off state of an input. In the chart, FF5 denotes replacing both sensors with FF5 control resulting in Off output; FF5+21 and FF5+17-30a denote one sensor replacement (emulating On+Off input states, resulting likewise in an Off output) and 21+17-30a represents an On+On combination, resulting in On output. c) Recombinase cascade eliminates the leakage. Sensor diagram is shown (top). The bar chart (middle) compares standard architecture with a Cre-only delayed architecture to a double-recombinase system.

Figure 4:
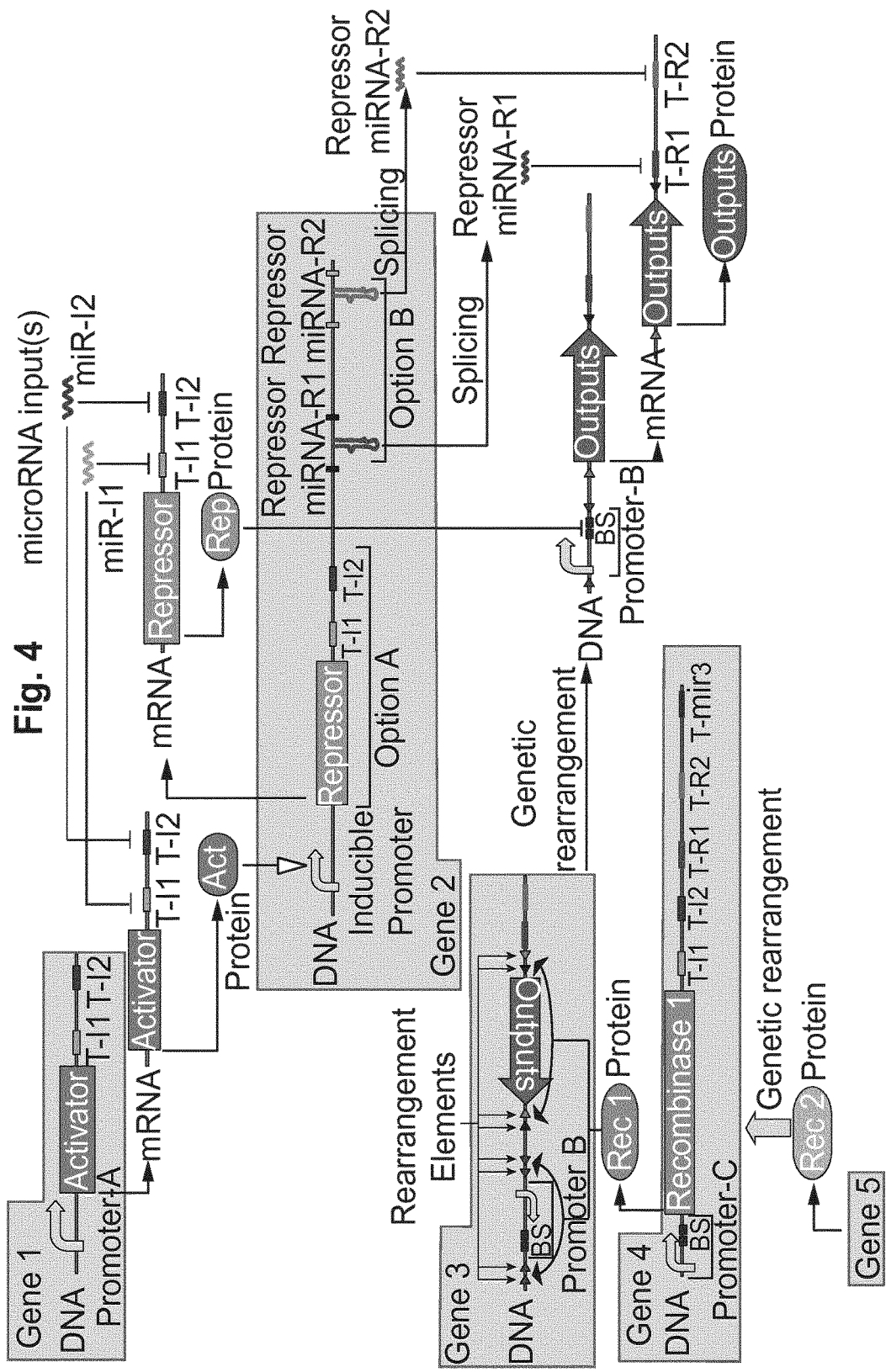

FIG. 4 shows an example of a preferred embodiment of the biosensor of the present invention. The boxed components are the genetic components, with the names gene 1 to gene 5. The other components are RNA and protein components that are generated from the genetic building blocks during intracellular operation. Filled arrows indicate transcription or translation, unless indicated otherwise. Hollow arrows denote promoter induction. Blunt arrows indicate repression via transcriptional repressor or microRNA (through RNA interference).

Figure 5:
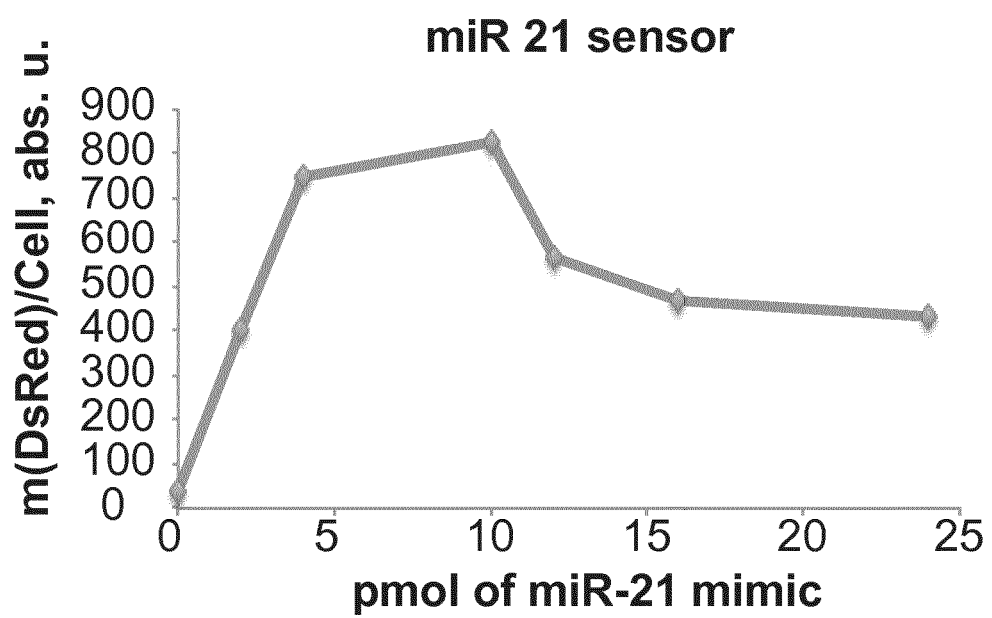

FIG. 5 shows the titration of miR-21 mimic. Repression release by miR-21 mimic of R-21 double-inversion module (300 ng of CMV-rtTA-21+300 ng of TRE-LacI-21-miR-FF4+300 ng of CAGop-DSRed-FF5-FF4).

FIG. 6 shows the reduction of output signal due to incomplete recombination. In a and b, line 1 represents standard output (CAGop-Lox2272-DsRed-LoxP-FF4) and line 2 represents delayed output (CAGop-Lox2272-LoxP-Reverse-DsRed-Lox2272-LoxP-FF4) both with the equivalent of 5 ng of EF1A-iCre. a) On state: miR-21 sensor+miR-21 mimic. b) Uncontrolled output constructs. c) Delay is increased with reduced Cre level. Lines 1 and 2 are the same as in b, line 3 represents backward-facing output with the equivalent of 30 ng of EF1A-Cre.

Figure 7:
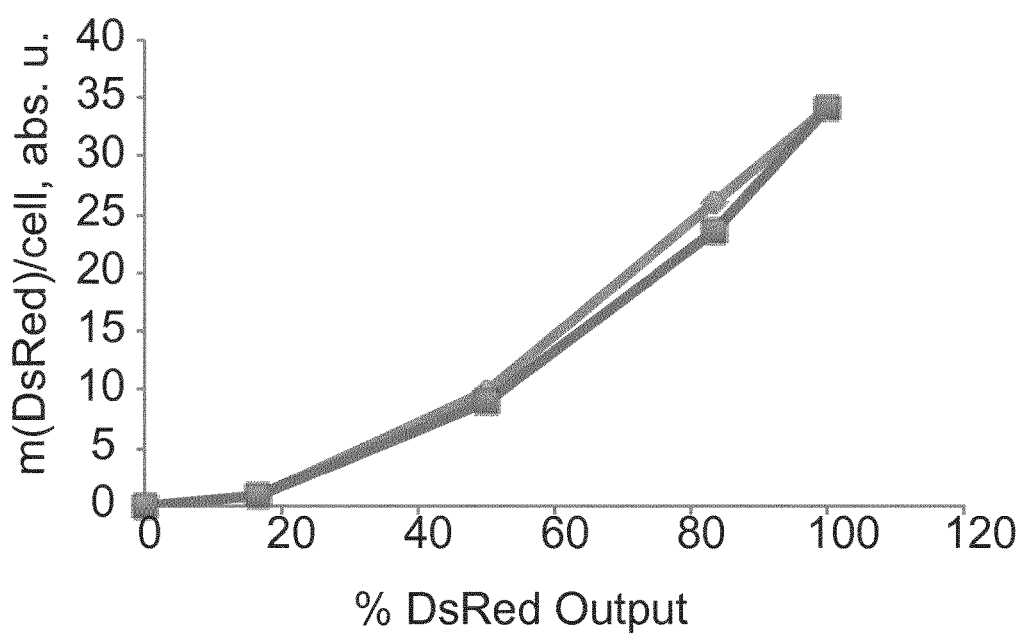

FIG. 7 shows the effect of antisense transcript on sensor output in the Off state. The repressor module (300 ng of CMV-rtTA-T21+300 ng of TRE-LacI-T21-miR-FF4) was kept constant. The output comprises a mixture of CAGop-Lox2272-DsRed-LoxP-FF4 and either CAGop-Lox2272-LoxP-Reverse-DsRed-Lox2272-LoxP-FF4 (Line 1) or pUBI-linker-NOS (Line 2). 100%=300 ng of total DNA.

FIG. 8 shows the effect of output composition on circuit performance. a-d) miR-21 sensor is characterized with different mixtures of forward- and backward-facing output genes in the absence of Cre, with the total amount of both outputs kept constant at 300 ng (see Table 3). The amount of forward-facing output is shown on the X axis. a) miR-21 sensor with negative control mimic. b) miR-21 sensor with miR-21 mimic. c) Dynamic range. d) Output alone. e,f) Dynamic range comparison (abs. u.:abs. u.) of delayed and mixed-output sensors with similar Off signals. e) Delayed sensor with 300 ng backward-facing output and 1.25 ng EF1A-Cre plasmid is bar 1 and mixed-output sensor (25 ng forward-facing output and 275 ng backward-facing output, no Cre) is bar 2. f) Delayed sensor with 300 ng backward-facing output and 10 ng of EF1A-Cre plasmid is bar 1 and mixed-output sensor (50 ng forward-facing output and 250 ng backward-facing output, no Cre) is bar 2.

Figure 9:
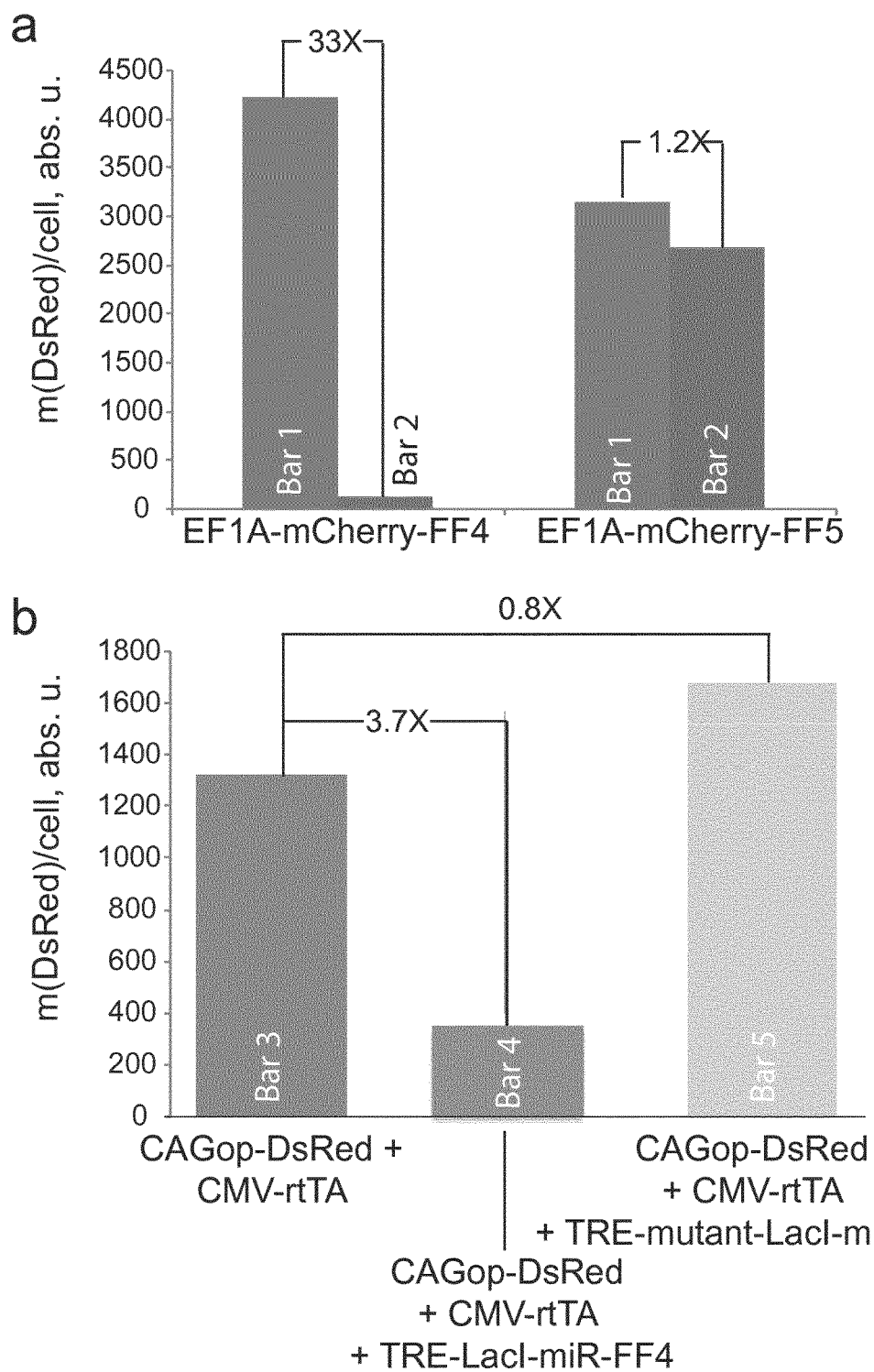

FIG. 9 shows the loss of function of mutant repressors. a) miR-FF4 loss of function measured with EF1A-mCherry-FF4 and EF1AmCherry-FF5 constructs. 300 ng of reporters are cotransfected with 300 ng of TRE-LacI-miR-mutant-FF4+300 ng CMV-rtTA (bars 1) or 300 ng TRELacI-FF4+300 ng CMV-rtTA (bars 2). b) LacI loss of function measured with CAGop-DsRed (300 ng), cotransfected with 600 ng CMV-rtTA (bar 3), 300 ng CMV-rtTA+300 ng TRE-LacI-miR-FF4 (bar 4), 300 ng CMVrtTA+300 ng TRE-mutant-LacI-miR-FF4 (bar 5).

Figure 10:
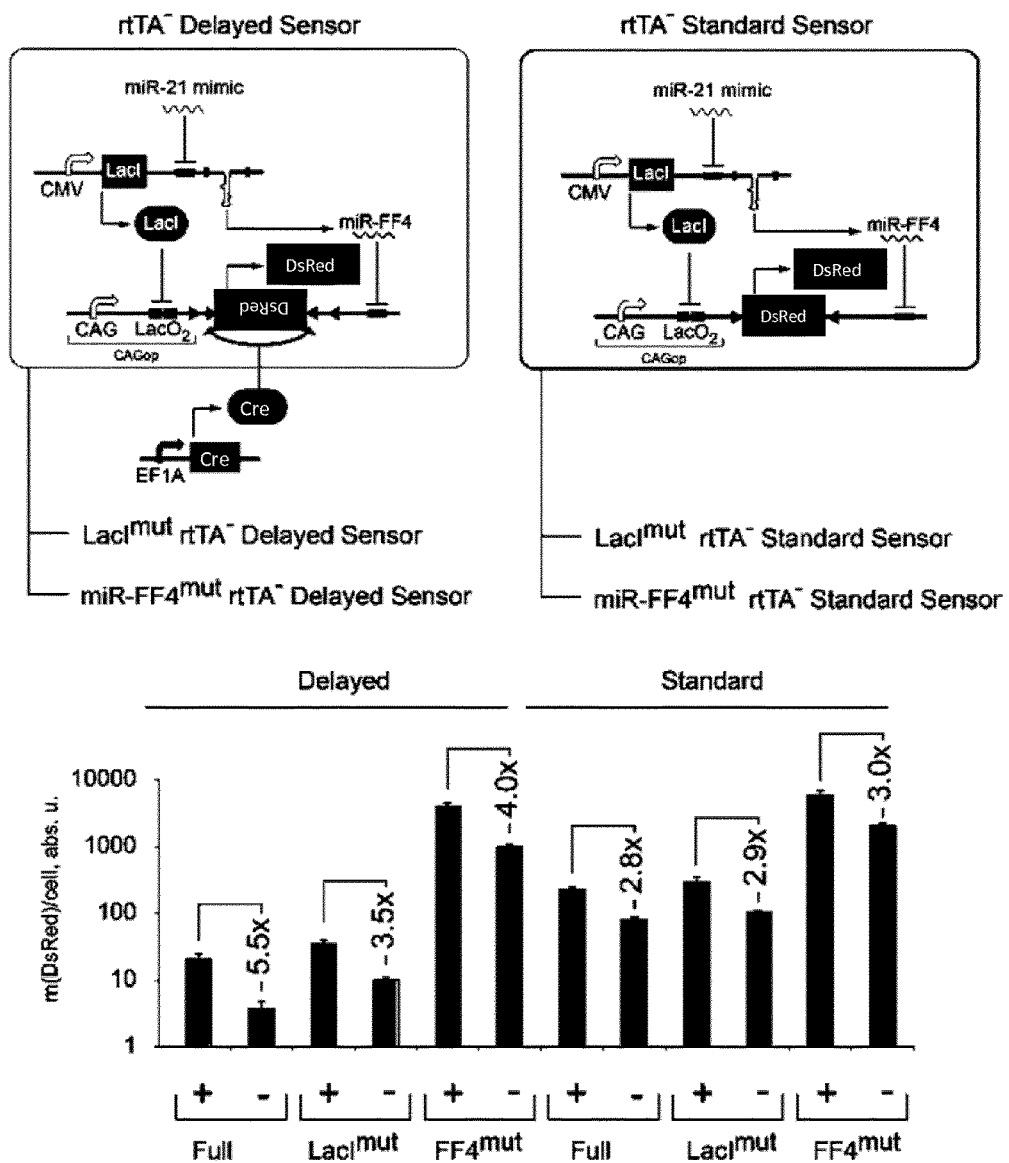

FIG. 10 shows the characterization of sensor variants without the activator. Circuit diagrams and their relative performance characteristics are shown. Transfection details are summarized in Table 1 (rtTA-experiments).

FIG. 11 shows the modularity of sensor design. Circuit schemes with swapped promoter (left) or output-coding sequence (right) are shown. Performance characterization is shown, comparing the standard and the delayed architectures. Transfection details are given in Table 2.7

Figure 12:
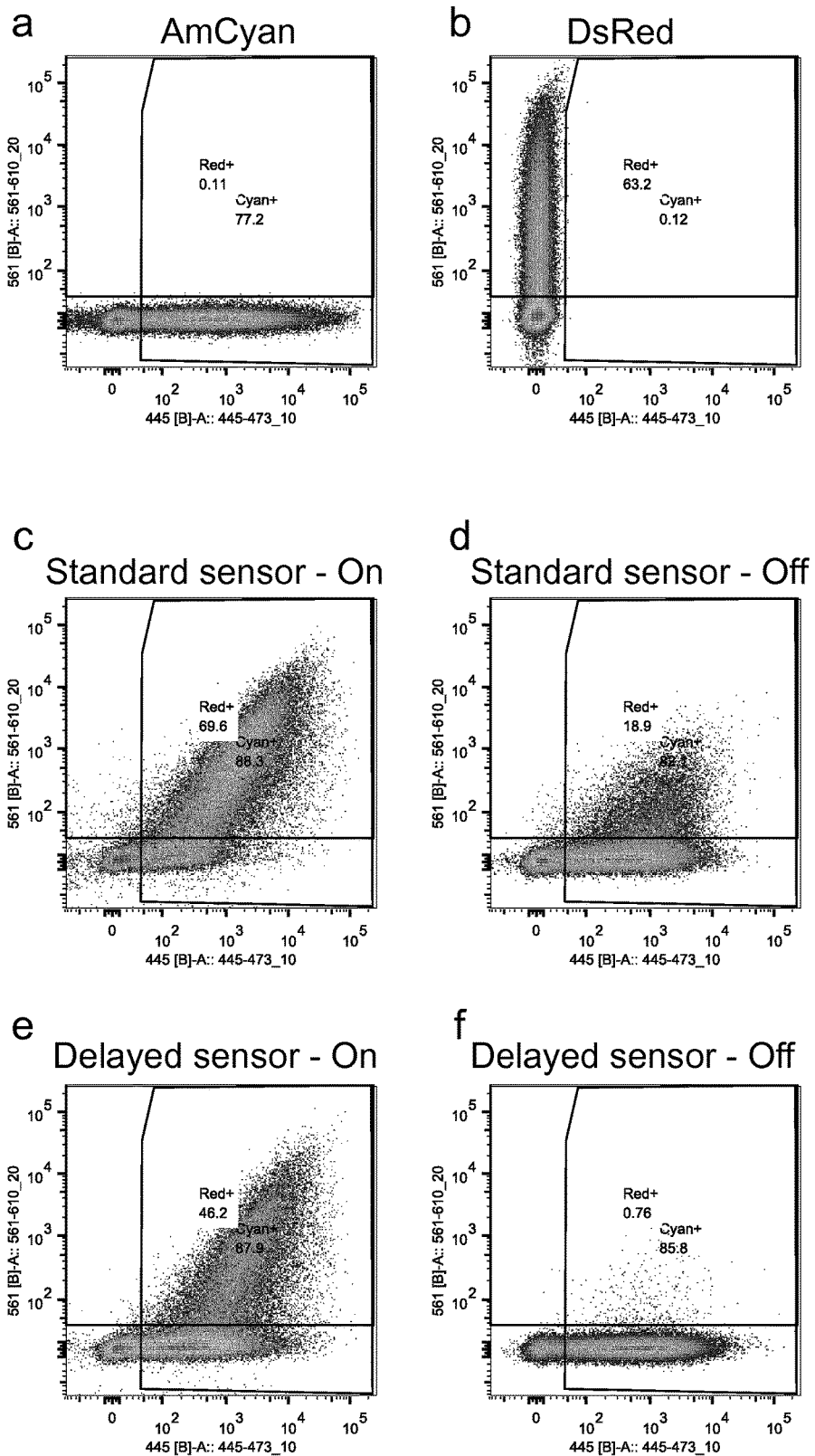

FIG. 12 shows Gating examples. a) DsRed$^+$ Gating is determined from AmCyan single color transfection with 99.9% DsRed$^+$ cells outside of the gate. b) AmCyan$^+$ Gating: Determined from DsRed single color transfection with 99.9% AmCyan$^+$ cells outside of the gate. c-f) Examples of gating applied to circuit analysis. c) Standard sensor with mi-R21 mimic. d) Standard sensor with negative control mimic. e) Delayed sensor with miR-21 mimic. f) Delayed sensor with negative control mimic.

Figure 13:
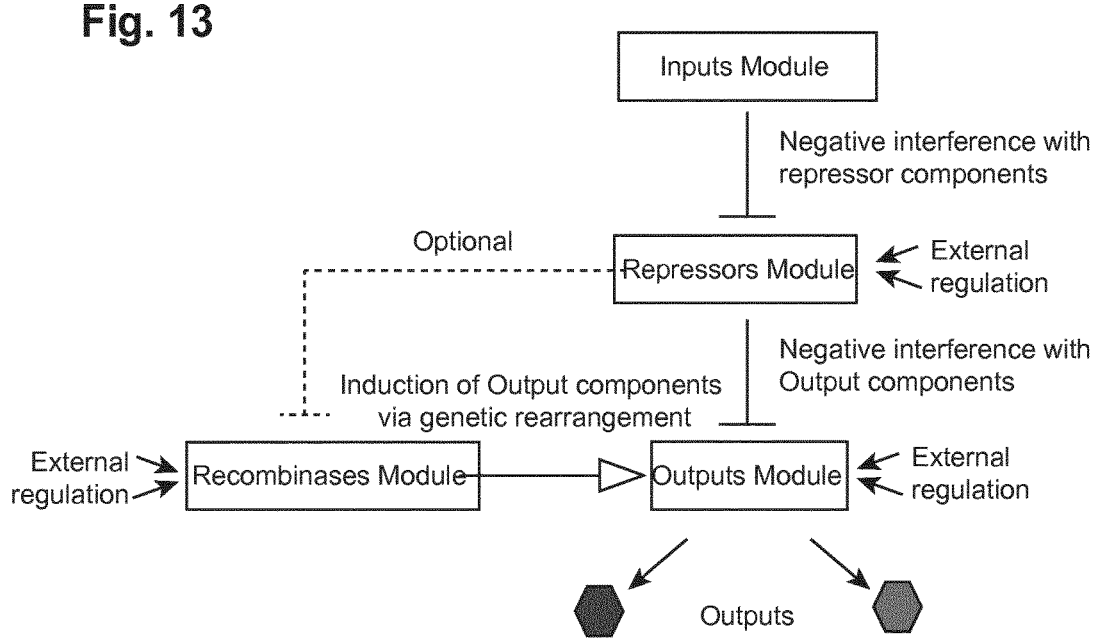

FIG. 13 shows a generalized scheme of the biosensor according to the invention. Each one of the repressors, outputs and recombinase modules contains one or more genes whose cumulative effect on other modules is shown.

CONTENTS AND RESULTS OBTAINED ACCORDING TO THE FIGURES

Previously, sensor leakiness in the Off state of biosensors was observed, even when the overall dynamic range (On: Off) was high. In this context, an assay system was established to study the causes for sensor leakiness and optimize its performance. The assay comprises HEK293 cells that naturally do not express many miRNAs, including miR-21. The focus was set on miR-21 input and miR-21 sensor with DsRed fluorescent output, generating sensor On state by co-transfecting a mimic of miR-21 into the cells. The optimal level of miR-21 mimic was determined in a titration experiment to be 10 pmol (FIG. 5). To evaluate the Off state, a similar molar amount of negative control miRNA mimic was used.

Using this assay, time-course measurements were performed of the sensor response following transient transfection, in both On and Off states. Sensor dynamics reveal that in both cases, the early expressing cells display very similar kinetics in the first few hours (0-5 h) before diverging (FIGS. 1c and 1d). This observation is qualitatively consistent with earlier findings in prokaryotic system regarding the delay between the expression of a repressor and the response of its target (see Dunlop et al., Nature Genet. 2008, 102, 3581-3586). Mean intensity of output expression in output-positive cells in the Off state also peaks around 5-6 h, suggesting that after this time period, there is enough repressor to prevent further increase in intensity. Thus it was hypothesized that a delay of 6-10 h in the output gene availability and the commencement of output gene expression might substantially reduce the leakage. While control over gene expression timing using transcriptional regulation is one option, the most drastic and at the same time, "clean" intervention would be to "withhold" the gene itself. This requires programmable, time-dependent modification in the circuit-encoding DNA that is best achieved through DNA-manipulating enzymes such as recombinases. Therefore, it was opted for a recombinase-driven inversion of the output coding region relative to its promoter. A Cre/Lox recombination system was engineered to delay output production, utilizing the FLEx switch that exploits the dual inversion and excision activity of the recombinase (see Schnutgen et al., Nat. Biotechnol. 2003, 21, 562-565). Using two pairs of incompatible Lox recombination sites, the coding region of the output sequence is stably and irreversibly inverted after Cre-mediated recombination (FIG. 2a). In a "delayed" sensor, the standard output construct is replaced with a backward-facing DsRed coding region; a constitutive Cre expression cassette is included with other circuit components. The delay introduced with this strategy amounts to 6-8 h, as can be seen from time-course flow cytometry data (FIG. 2b), As a result, a dramatic effect on the sensor Off state was observed (FIGS. 2c-2e)—virtually all the leakage is eliminated, while the On state is only moderately reduced. This reduction in the On state can be largely explained by incomplete inversion of the backward-facing output, probably due to imperfect cotransfection (FIGS. 6a and 6b). There is an overall improvement of about 30-fold in the dynamic range of the sensor as shown in FIG. 2c. It was noted parenthetically that cotransfection of negative control mimic, which is a proper Off measurement while using miR-21 mimic, increases the Off state of the standard sensor and to a less extent in the delayed sensor. Yet even when negative control mimic is withheld (Line 1 in FIG. 2c), there is about an order of magnitude improvement in the Off state.

It was then proceeded to investigate the effect of recombinase amount on the leakage and the dynamic range of the sensor. The On signal fits the Hill function with n=1 and apparent "$EC_{50}$" in the order of 2 ng regardless of the quantitation method (FIG. 2f). The Off output depends on the amount of recombinase in an almost linear fashion (Off~$[Cre]^{0.77}$) (FIG. 2f), resulting in On:Off ratio at lower recombinase levels reaching >2000-fold (FIG. 2g). The mean intensity of DsRed-expressing cells in the On state does not depend on Cre amount (FIG. 2h). Therefore, the decrease in the total On signal in the delayed sensor results from the reduced proportion of DsRed-expressing cells caused by imperfect cotransfection of the output and the recombinase genes at very low Cre levels. At the same time, the improved Off output with reduced Cre is likely due to increased delay (FIG. 6c). Following optimization, it was decided to use 5 ng of Cre-expressing plasmid in the experiments that follow, unless indicated otherwise.

Two additional explanations for the observed effect were tested. First, it was evaluated whether the anti-sense DsRed transcripts generated from backward-facing output genes sequester forward-facing output transcripts. However, a discernible effect was not measured as measured against "filler" DNA (FIG. 7). Second, it was checked whether the effect could be attributed simply to the reduction of the output gene dosage relative to double-inversion module genes due to incomplete recombination. To address this possibility, sensor performance with different ratios of inverted and forward-facing output genes was measured, in the absence of Cre recombinase. Data in FIG. 8 show that while the Off state improves when the forward-facing output is reduced, the On output is reduced by comparable fraction, leaving the On:Off ratio largely constant. Thus using recombinaseinduced delay maintains high output levels in the On state without accompanying increase of leakage in the Off state.

The above data support the hypothesis that the delay introduced by the recombinase eliminates the leakage by allowing the double-inversion module to generate enough repressor molecules prior to the commencement of output expression. Next it was asked which molecular features of the double-inversion module contribute most to the effect. The repressor is a combined transcriptional/post-transcriptional unit that uses LacI and artificial microRNA miR-FF4, respectively. Thus either the LacI or the miR-FF4 component (FIGS. 3a and 9) was mutated and sensor performance in both standard and delayed configurations was measured (FIG. 3a). The data show that while LacI-miR-FF4 combination is the best performer, the LacI mutant still generates most of the repression capacity via miR-FF4. In the delayed configuration it exhibits a dynamic range of more than two orders of magnitude, and likewise in the standard setting the effect of LacI removal is relatively minor. On the other hand, removing miR-FF4 has a major detrimental effect on both delayed and standard architectures.

In order to further improve the understanding of sensor mechanism, the activator rtTA was removed and the TRE promoter of LacI-miR-FF4 construct was replaced with a constitutive CMV promoter (FIG. 10). It was conjectured that removing rtTA induction would accelerate the expression of LacI and miR-FF4, thus improving the Off state to the level observed otherwise with Cre-induced delay. However, only a two-fold improvement of the Off state relative to full and LacI$^{mut}$ standard sensors was found. It was also expected that in LacI mutants, the On state will be identical to the Off state due to the fact that miR-FF4 processing presumably happens before miR-FF4 containing transcript can be knocked-down by miR-21. Interestingly, a weak but reproducible effect was observed even when LacI was mutated. The effect was measured both in the standard and delayed configurations. One explanation is that in dividing cells such as HEK, the strict separation between nucleus and cytoplasm is not maintained all the time and thus even unspliced LacI-miR-FF4 transcript could be targeted by miR-21. To summarize, strong repression can be achieved without transcriptional activator but the latter is essential for the sensor 'de-repression' to high On state and for high dynamic range.

The applicability of the above approach was explored in a number of additional scenarios. First, a LacI-controlled CAGop promoter was replaced with CMV; second the DsRed output gene was replaced with ZsYellow (FIG. 11). In both cases there was a large improvement in the Off state, as expected. Replacing DsRed with ZsYellow delivered very similar performance, suggesting that the sensor can be used to control different output genes. Interestingly, CMV promoter proved difficult to de-repress. In a fully modular system one would expect the effect to be roughly comparable to the LacI$^{mut}$ circuits. However, in the standard configuration the effect decreases from 15× to 3×, and in the delayed one from 150× to 15×.

It was also checked if the new sensor could be incorporated in larger networks such as previously-published HeLa cell classifier (see Xie et al., Science 2011, 333, 1307-1311). To this end, an un-optimized measurement of the logic AND behavior of the circuit under standard and delayed configurations was performed (FIG. 3b). Note that in this case the inputs are endogenous miR-21, miR-17 and miR-30a. Data show large improvement in the Off state similar to that observed in our model HEK system and overall >100-fold On:Off ratio in the best case (both inputs turned off). At the same time, there was a reduction in the On state; however, this reduction could be explained entirely by incomplete Cre-induced inversion under these particular conditions.

Finally, it was examined whether even stronger delay can further improve the Off state. a second site-specific recombinase Flp and Flp-compatible FLEx cassette was used to flank the Cre gene (FIG. 3c). To increase cotransfection of both recombinases, high amount of Cre-expressing plasmid (25 ng) was used in the standard, delayed (Cre) and Flp-Cre strategies. In a side-by-side comparison there is a 20-fold improvement over one-recombinase case with similar plasmid amount with the dynamic range close to 2,000. Fine-tuning is likely to improve the range further.

EXAMPLES

General Materials

RNA mimic of human miR-21 and negative control miRNA were purchased from Dharmacon RNAi Technology (Thermo Fisher scientific, Waltham, Mass. 02451 USA). miR-21 mimic (cat # C-300492-03-0005) is double-stranded RNA that mimics the function of human miRNA-21 (MI0000077). Negative Control mimic (cat # CN-001000-01-05) is based on a mix of C. Elegans miRNA sequences.

Example 1—Cell Culture and Transfection

HEK293 (293-H) cell line was purchased from Invitrogen™ (Life Techonlogy, a Thermo Fisher scientific Brand, Waltham, Mass. 02451, USA, cat #11631-017). HEK293 cells were cultured in RPMI-1640 medium (Gibco™|Life Technologies, a Thermo Fisher Scientific Brand, Waltham, Mass. 02451, USA, cat # A10491-01) supplemented with 10% FBS (Sigma-Aldrich, Saint-Louis, Mo. 63103 USA), 0.045 g/mL of penicillin and 0.045 g/ml streptomycin at 37° C., 100% humidity and 5% $CO_2$. Lipofectamine 2000 transfection reagent (Invitrogen™|Life Technologies, a Thermo Fisher Scientific Brand, Waltham, Mass. 02451 USA) was used in HEK293 experiments. $1.5 \times 10^5$ HEK293 cells were seeded in 1 mL RPMI 1640 complete medium (Gibco™|Life Technologies, a Thermo Fisher Scientific Brand, Waltham, Mass. 02451 USA) into each well of 12-well uncoated plastic plate (Nunc™|Life Technologies, a Thermo Fisher Scientific Brand, Waltham, Mass. 02451 USA) and grown for about 24 h. 2.8 µl of Lipofectamine 2000 were added to each sample as described in the manual using Optimem™ (Life Technologies, a Thermo Fisher Scientific Brand, Waltham, Mass. 02451 USA) to resuspend DNA (100 µL/sample) and incubation reagent (100 µL/sample). Medium was changed before transfection with doxycycline (Fluka|Sigma-Aldrich, Saint-Louis, Mo. 63103 USA; cat #44577-5G) to a final dilution of 1 µg/mL.

HeLa cell line was purchased from ATCC (Manassas, Va. 20108 USA; cat # CCl-2). Hela cells were cultures in DMEM medium (Gibco™|Life Technologies, a Thermo Fisher Scientific Brand, Waltham, Mass. 02451 USA; cat #11966-025) supplemented with 10% FBS (Sigma-Aldrich, Saint-Louis, Mo. 63103), 4.5 g D-Glucose/L, 1 mM non-essential amino acids (Gibco™|Life Technologies, a Thermo Fisher Scientific Brand, Waltham, Mass. 02451 USA; cat #11140-035), 0.045 g/mL of penicillin and 0.045 g/mL streptomycin at 37° C., 100% humidity and 5% $CO_2$. Effectene transfection reagent (Qiagen, Dusseldorf, D-45822 Germany) was used in Hela experiments. $1 \times 10^5$ Hela cells were seeded in 1 mL high-Glucose DMEM (Gibco™|Life Technologies, a Thermo Fisher Scientific Brand, Waltham, Mass. 02451 USA; cat #11966-025) complete medium into each well of 12-well uncoated plastic plate (Nunc™|Life Technologies, a Thermo Fisher Scientific Brand, Waltham, Mass. 02451 USA) and grown for about 24 h. 2.4 μL Enhancer and 6 μL Effectene (Qiagen, Dusseldorf, D-45822 Germany) were sequentially added to each DNA mixture as described in the manual, followed by adding 400 μL high-glucose DMEM complete media with 1 μg/mL doxycycline (Fluka|Sigma-Aldrich, Saint-Louis, Mo. 63103 USA; cat #44577-5G). Growth medium in the overnight-incubated plates with HeLa cells was replaced with 800 high-glucose DMEM complete media with 1 μg/mL doxycycline. The DNA preparation was added to cells and incubated for 3 h at 37° C./5% $CO_2$. After 3 h incubation, media containing transfection complexes were replaced with fresh high-glucose-DMEM complete media supplemented with 1 μg/mL doxycycline. Transfected cells were incubated for 3 days before flow cytometry analysis. All reported data are averaged values of three to five biological replicas. The error bars represent +/−one standard deviation.

Example 2—Flow Cytometry Measurements

Fortessa flow analyzers (BD Biosciences, Franklin Lakes, N.J. 07417 USA) were used for fluorescence flow analysis. DsRed was measured using 561 nm Laser, a 600 nm Longpass filter and a 610/20 emission filter with a PMT at 280 V. AmCyan and Cerulean were measured using 445 nm Laser and 473/10 emission filter with a PMT at 280 V. ZsYellow was measured using 480 nm Laser, a 505 Longpass filter and a 542/27 emission filter with a PMT at 220 V. The improvement of the delayed sensor over standard architecture are not sensitive to specific PMT values in the DsRed channel as shown FIG. 12.

Example 3—Time Course Measurements

Transfections were done in 24-well uncoated plastic plate (Nunc™|Life Technologies, a Thermo Fisher Scientific Brand, Waltham, Mass. 02451 USA) with seeding and transfection reagent scaled down by a factor of two (See Cell Culture and Transfection section). 21× master mix for each transfection was prepared and 1× of each master mix was added to each well individually. Each time course data point comes from a separate transfected well.

Example 4—Data Analysis

Scatter plots and bar charts in all the figures were generated as follows. Gating for % $DsRed^+$ was determined from AmCyan single color transfection with 99.9% $DsRed^+$ cells outside the gate. Gating for % $AmCyan^+$ was determined from DsRed single color transfection with 99.9% $AmCyan^+$ cells outside the gate. Gating examples are shown in FIG. 12. For each sample, the frequency of DsRed-positive cells (% $DsRed^+$), the mean DsRed value in $DsRed^+$ cells, mean ($DsRed^+$), and the frequency of AmCyan positive cells (% $AmCyan^+$) were calculated. The average signal per transfected cell, denoted as m(DsRed)/Cell, abs. u. in the charts, was calculated as: $mean(DsRed^+)*(\% DsRed^+)/(\% AmCyan^+)$. The average signal without normalization, denoted as Σ DsRed a.u. in the charts, was calculated as: $mean(DsRed^+)*(\% DsRed^+)$.

The frequency of DsRed cells denoted as $DsRed^+/AmCyan^+$ in the left panels in FIG. 2f was calculated as: (% $DsRed^+$) (% $AmCyan^+$).

The relative expression of DsRed signal denoted as m(DsRed)/Cell rel. u. in the middle panels of FIG. 2f, was calculated as:

$$mean(DsRed^+)*(\% DsRed^+)/mean(AmCyan^+)*(\% AmCyan^+).$$

Example 5—Plasmid DNA Constructs

Standard molecular biology techniques were used. Oligonucleotides sequences used to prepare the plasmid DNA constructs are listed in Table 4.

CAGop-Lox2272-LoxP-Reverse-DsRed-Lox2272-LoxP-FF4: DsRed was amplified from CAGop-DsRed-FF5-FF4 with PR1 and PR2. The PCR product replaced eGFP in CAG-Lox2272-LoxP-Reverse-eGFP-Lox2272-LoxP (Addgene, Cambridge, Mass. 02139 USA; cat #28304) using XhoI and KpnI. CAG-Lox2272-LoxP-Reverse-DsRed-Lox2272-LoxP has been amplified with PR3 and PR4, and the PCR product has replaced DsRed with Lox2272-LoxP-Reverse-DsRed-Lox2272-LoxP in CAGop-DsRed-FF5-FF4 using NheI and HindII.

CAGop-Lox2272-DsRed-LoxP-FF4: In vitro recombination of 250 ng of CAGop-Lox2272-LoxP-Reverse-DsRed-Lox2272-LoxP-FF4, using 1 unit of Cre recombinase (NEB, Ipswich, Mass. 01938 USA) during 1 h at 37° C.

TRE-LacI-T21-mi R-mutant_FF4: miR-FF4 in TRE-LacI-T21-miR-FF4 (Xie et al.) was replaced with mutant sequence (gBlock1 from Integrated DNA Technologies, BVBA, Leuven, B-3001 Belgium) using with HindIII and SalI.

TRE-mutant-LacI-FF4: Insertion of adenosine nucleotide after LacI start codon to produce frameshift mutation. TRE-LacI-T21-miR-FF4 was amplified with phosphorylated PR5 and PR6, and PCR product was ligated.

CAGop-Lox2272-LoxP-Reverse-ZsYellow-Lox2272-LoxP-FF4 was produced with 3 parts assembly. CAGop-Lox2272-LoxP-Reverse-DsRed-Lox2272-LoxP-FF4 was digested with XhoI and KpnI, ZsYellow was amplified from commercial plasmid pZsYellow1-N1 (Clontech, a Takara Bio Company, Otsu, Shiga 520-2193 Japan) with PR7 and PR8 and digested with XhoI and AseI, Lox2272-LoxP amplified from CAGop-Lox2272-LoxP-Reverse-DsRed-Lox2272-LoxP-FF4 with PR9 and PR10 and digested with AseI and KpnI. The 3 fragments were ligated overnight at 4° C.

CAGop-Lox2272-ZsYellow-LoxP-FF4: In vitro recombination of 250 ng of CAGop-Lox2272-LoxP-Reverse-ZsYellow-Lox2272-LoxP-FF4, using 1 unit of Cre recombinase (NEB, Ipswich, Mass. 01938 USA) during 1 hour at 37° C.

EF1A-iCre is reported in Prochazka et al., Nat Commun. 2014, 5, 4729.

CMV-Lox2272-LoxP-Reverse-DsRed-Lox2272-LoxP-FF4: CMV promoter from Advanced-tTA commercial plasmid (Clontech, a Takara Bio Company, Otsu, Shiga 520-2193 Japan) was digested with SpeI and XbaI. It was used to replace CAGop promoter from CAGop-Lox2272-LoxP-Reverse-DsRed-Lox22 72-LoxP-FF4 using SpeI and NheI.

CMV-Lox2272-DsRed-LoxP-FF4 was prepared using the same strategy as CMV-Lox2272-LoxP-Reverse-DsRed-Lox2272-LoxP-FF4, but with CAGop-Lox2272-DsRed-LoxP-FF4 as parental plasmid.

CMV-LacI-T21-miR-FF4: LacI-T21-miR-FF4 was removed from TRE-LacI-T21-miR-FF4 with NheI and PciI. The fragment was used to exchange tTA in Advanced-tTA commercial plasmid (Clontech, a Takara Bio Company, Otsu, Shiga 520-2193 Japan) using XbaI and PciI.

CMV-mutant_LacI-T21-mi R-FF4: mutant-LacI-T21-miR-FF4 was digested from TRE-mutant-LacI-T21-miR-FF4 with NheI and PciI. The fragment was used to replace tTA in Advanced-tTA commercial plasmid (Clontech, a Takara Bio Company, Otsu, Shiga 520-2193 Japan) using XbaI and PciI.

CMV-LacI-T21-miR-mutant_FF4: Laci-T21-miR-mutant_FF4 was digested from TRE-LacI-T21-miR-mutant_FF4 with NheI and PciI. The fragment was used to exchange tTA in Advanced-tTA commercial plasmid (Clontech, a Takara Bio Company, Otsu, Shiga 520-2193 Japan) using XbaI and PciI.

CAG-ERT2-iCre-ERT2 (pNL125) was obtained from Addgene (Cambridge, Mass. 02139 USA; cat #13777).

CMV-FRT-f3-Reverse_iCre-FRT-F3: CMV-FRT-F3-Reverse_Citrine-miR-145-FRT-F3 is described in Prochazka et al., Nat Commun. 2014, 5, 4729. iCre has been PCR amplified from EF1A-iCre using PR11. The PCR product was used to replace Citrine-miR-145 in CMV-FRT-F3-Reverse_Citrine-miR-145-FRT-F3 using HindIII and SbfI.

EF1A-Cerulean: Cerulean was PCR amplified with PR13 and PR14 from CMV-Brainbow-2 (Addgene, Cambridge, Mass. 02139, United States; cat #18723) and inserted in EF1A-eGFP (Addgene, Cambridge, Mass. 02139, United States; cat #11154) using EcoRI and EagI.

CAG-Cerulian: Cerulean was extracted from EF1A-Cerulean with EcoRI and BglIII and exchange AmCyan in CAG-AmCyan digested with EcoRI and BamHI.

EF1A-Flp0 is reported in Prochazka et al., Nat Commun. 2014, 5, 4729.

Plasmids reported in Xie et al, Science 2011:
CAG-AmCyan, CAGop-DsRed-FF4, CAGop-DsRed, TRE-LacI T21-miR-FF4, TRE-LacI-T17-T30a-miR-FF4, TRE-LacI-FF5-miR-FF4, CMV-rtTAT21, CMV-rtTA T17-T30a, CMV-rtTA-FF5, pUBI-linker-NOS.

TABLES

Table 1 shows the transfection configuration used for mutant sensors shown in FIG. 3a and FIG. 10. ng-amount of plasmids and pmol of micro RNA mimic are indicated. Transfections are performed in 12-well plates.

Table 2 shows the transfection configuration used for output modularity shown in FIG. 11. ng-amount of plasmids and pmol of micro RNA mimic are indicated. Transfections are performed in 12-well plates.

Table 3 shows the transfection configuration used for output titration shown in FIG. 8. ng-amount of plasmids and pmol of microRNA mimic are indicated. Transfections are performed in 12-well plates.

Table 4 shows the oligonucleotide sequences used for plasmid DNA constructs preparation.

TABLE 1

| | Full wild Type (ON) | Full wild Type (OFF) | Full mutant LacI (ON) | Full mutant LacI (OFF) | Full mutant miR-FF4 (ON) | Full mutant miR-FF4 (OFF) | tTA-wild Type (ON) | tTA-wild Type (OFF) | tTA-mutant LacI (ON) | tTA-mutant LacI (ON) | tTA-mutant miR-FF4 (ON) | tTA-mutant miR-FF4 (OFF) |
|---|---|---|---|---|---|---|---|---|---|---|---|---|
| *Standard miR-21 Sensor* | | | | | | | | | | | | |
| CAGop-Lox2272-DsRed-LoxP-FF4 | 300 | 300 | 300 | 300 | 300 | 300 | 300 | 300 | 300 | 300 | 300 | 300 |
| CMV-rtTA-T21 | 300 | 300 | 300 | 300 | 300 | 300 | 300 | 300 | 300 | 300 | 300 | 300 |
| TRE-LacI-T21-miR-FF4 | 300 | 300 | | | | | | | | | | |
| TRE-muant-LacI-T21-miR-FF4 | | | 300 | 300 | | | | | | | | |
| TRE-LacI-T21-miR-mutant-FF4 | | | | | 300 | 300 | | | | | | |
| CMV-LACI-miR-FF4 | | | | | | | 540 | 540 | | | | |
| CMV-mutant-LACI-miR-FF4 | | | | | | | | | 540 | 540 | | |
| CMV-LACI-miR-mutant-FF4 | | | | | | | | | | | 540 | 540 |
| EF1A-iCre | 5 | 5 | 5 | 5 | 5 | 5 | 5 | 5 | 5 | 5 | 5 | 5 |
| CAG-AmCyan | 300 | 300 | 300 | 300 | 300 | 300 | 300 | 300 | 300 | 300 | 300 | 300 |
| miR-21 mimic | 10 pMol | | 10 pMol | | 10 pMol | | 10 pMol | | 10 pMol | | 10 pMol | |
| Negative Control mimic | | 10 pMol | | 10 pMol | | 10 pMol | | 10 pMol | | 10 pMol | | 10 pMol |
| *Delayed miR-21 Sensor* | | | | | | | | | | | | |
| CAGop-Lox2272-LoxP-Reverse-DsRed-Lox2272-LoxP-FF4 | 300 | 300 | 300 | 300 | 300 | 300 | 300 | 300 | 300 | 300 | 300 | 300 |
| CMV-rtTA-T21 | 300 | 300 | 300 | 300 | 300 | 300 | 300 | 300 | 300 | 300 | 300 | 300 |
| TRE-LacI-T21-miR-FF4 | 300 | 300 | | | | | | | | | | |
| TRE-muant-LacI-T21-miR-FF4 | | | 300 | 300 | | | | | | | | |
| TRE-LacI-T21-miR-mutant-FF4 | | | | | 300 | 300 | | | | | | |
| CMV-LACI-miR-FF4 | | | | | | | 540 | 540 | | | | |
| CMV-Mutant-LACI-miR-FF4 | | | | | | | | | 540 | 540 | | |
| CMV-LACI-miR-mutant-FF4 | | | | | | | | | | | 540 | 540 |
| EF1A-iCre | 5 | 5 | 5 | 5 | 5 | 5 | 5 | 5 | 5 | 5 | 5 | 5 |
| CAG-AmCyan | 150 | 150 | 150 | 150 | 150 | | 150 | 150 | | | | 300 |
| miR-21 mimic | 10 pMol | | 10 pMol | | 10 pMol | | 10 pMol | | 10 pMol | | 10 pMol | |
| Negative Control mimic | | 10 pMol | | 10 pMol | | 10 pMol | | 10 pMol | | 10 pMol | | 10 pMol |

TABLE 2

| | Standard miR-21 Sensors | | | | | |
|---|---|---|---|---|---|---|
| | CAGop-DsRed output (ON) | CAGop-DsRed output (OFF) | CAGop-ZsYellow output (ON) | CAGop-ZsYellow output (OFF) | CMV-DsRed output (ON) | CMV-DsRed output (OFF) |
| CAGop-Lox2272-DsRed-LoxP-FF4 | 300 | 300 | | | | |
| CAGop-Lox2272-ZsYellow-LoxP-FF4 | | | 300 | 300 | | |
| CMV-Lox2272-DsRed-LoxP-FF4 | | | | | 300 | 300 |
| CAGop-Lox2272-LoxP-Reverse-DsRed-Lox2272-LoxP-FF4 | | | | | | |
| CAGop-Lox2272-LoxP-Reverse-ZsYellow-Lox2272-LoxP-FF4 | | | | | | |
| CMV-Lox2272-LoxP-Reverse-DsRed-Lox2272-LoxP-FF4 | | | | | | |
| CMV-rtTA-T21 | 300 | 300 | 300 | 300 | 300 | 300 |
| TRE-LacI-T21-miR-FF4 | 300 | 300 | 300 | 300 | 300 | 300 |
| EF1A-iCre | 5 | 5 | 5 | 5 | 5 | 5 |
| CAG-AmCyan | 300 | 300 | 300 | 300 | 300 | 300 |
| miR-21 mimic | 10 pMol | | 10 pMol | | 10 pMol | |
| Negative Control mimic | | 10 pMol | | 10 pMol | | 10 pMol |

| | Delayed miR-21 Sensors | | | | | |
|---|---|---|---|---|---|---|
| | CAGop-DsRed output (ON) | CAGop-DsRed output (OFF) | CAGop-ZsYellow output (ON) | CAGop-ZsYellow output (OFF) | CMV-DsRed output (ON) | CMV-DsRed output (OFF) |
| CAGop-Lox2272-DsRed-LoxP-FF4 | | | | | | |
| CAGop-Lox2272-ZsYellow-LoxP-FF4 | | | | | | |
| CMV-Lox2272-DsRed-LoxP-FF4 | | | | | | |
| CAGop-Lox2272-LoxP-Reverse-DsRed-Lox2272-LoxP-FF4 | 300 | 300 | | | | |
| CAGop-Lox2272-LoxP-Reverse-ZsYellow-Lox2272-LoxP-FF4 | | | 300 | 300 | | |
| CMV-Lox2272-LoxP-Reverse-DsRed-Lox2272-LoxP-FF4 | | | | | 300 | 300 |
| CMV-rtTA-T21 | 300 | 300 | 300 | 300 | 300 | 300 |
| TRE-LacI-T21-miR-FF4 | 300 | 300 | 300 | 300 | 300 | 300 |
| EF1A-iCre | 5 | 5 | 5 | 5 | 5 | 5 |
| CAG-AmCyan | 300 | 300 | 300 | 300 | 300 | 300 |
| miR-21 mimic | 10 pMol | | 10 pMol | | 10 pMol | |
| Negative Control mimic | | 10 pMol | | 10 pMol | | 10 pMol |

TABLE 3

| | 0% Ouptut | | 8.3% Ouptut | | 16.7% Ouptut | | 33.3% Output | | 50% Output | | 66.7% Output | | 83.3% Output | | 91.7% Output | | 100% Output | |
|---|---|---|---|---|---|---|---|---|---|---|---|---|---|---|---|---|---|---|
| CAGop-Lox2272-DsRed-LoxP-FF4 | 0 | 0 | 25 | 25 | 50 | 50 | 100 | 100 | 150 | 150 | 200 | 200 | 250 | 250 | 275 | 275 | 300 | 300 |
| CAGop-Lox2272-LoxP-Reverse-DsRed-Lox2272-LoxP-FF4 | 300 | 300 | 275 | 275 | 250 | 250 | 200 | 200 | 150 | 150 | 100 | 100 | 50 | 50 | 25 | 25 | 0 | 0 |
| CMV-rtTA-T21 | 300 | 300 | 300 | 300 | 300 | 300 | 300 | 300 | 300 | 300 | 300 | 300 | 300 | 300 | 300 | 300 | 300 | 300 |
| TRE-LacI-T21-miR-FF4 | 300 | 300 | 300 | 300 | 300 | 300 | 300 | 300 | 300 | 300 | 300 | 300 | 300 | 300 | 300 | 300 | 300 | 300 |
| miR-21 mimic | 10 | | 10 | | 10 | | 10 | | 10 | | 10 | | 10 | | 10 | | 10 | |
| Negative Control mimic | | 10 | | 10 | | 10 | | 10 | | 10 | | 10 | | 10 | | 10 | | 10 |
| CAG-AmCyan | 300 | 300 | 300 | 300 | 300 | 300 | 300 | 300 | 300 | 300 | 300 | 300 | 300 | 300 | 300 | 300 | 300 | 300 |

TABLE 4

| OligoName | Oligo Sequence |
| --- | --- |
| PR1 SEQ ID NO: 1 | 5'-ACTGTGACGGTACCATGGCCTCCTCCGAGGACGT-3' |
| PR2 SEQ ID NO: 2 | 5'-ACTGTGACCTCGAGCTACAGGAACAGGTGGTGGCGG-3' |
| PR3 SEQ ID NO: 3 | 5'-ACTGTGACGCTAGCTTGGCAAAGAATTGGATCCCC-3' |
| PR4 SEQ ID NO: 4 | 5'-TGGCAATGCCCCAACCAGTGGGGGTTGC-3' |
| PR5 SEQ ID NO: 5 | 5'-P-AACCAGTAACGTTATACGATGTCGC-3' |
| PR6 SEQ ID NO: 6 | 5'-P-CATGGTGGGAGGGTACCTCGCTA-3' |
| PR7 SEQ ID NO: 7 | 5'-GGTACTTCGGCGCGCCCCGGTCGCCACCATGGCCCAC-3' |
| PR8 SEQ ID NO: 8 | 5'-GGTACTTCCTCGAGCGGCCGCTTCAGGCCAGGGCGC-3' |
| PR9 SEQ ID NO: 9 | 5'-GCCACGGGCGCGCCGCTAGAGCTCGCGGTGCCGAATTCT-3' |
| PR10 SEQ ID NO: 10 | 5'-GGAGCAGGTACCGTCGACTGCAGAATTCG-3' |
| PR11 SEQ ID NO: 11 | 5'-GGACTGACAAGCTTGATCCGCCGCCACCATGGTGC-3' |
| PR12 SEQ ID NO: 12 | 5'-GGACTGTGCCTGCAGGGTTCAGTCCCCATCCTCGAGCAGCC-3' |
| PR13 SEQ ID NO: 13 | 5'-ATATATGAATTGTTAATTGACAGCCAGCATGC-3' |
| PR14 SEQ ID NO: 14 | 5'-TATATCGGCCGCGCTTTACTTGTACAGCTCGTC-3' |
| gBlock 1 SEQ ID NO: 15 | 5'-CAAGATAGCAGGGAAGTCAAGCTTGAGGTGAGTATGTGCTCGCTTCG GCAGCACATATACTATGTTGAATGAGGCTTCAGTACTTTACAGAATCGT TGCCTGCACATCTTGGAAACACTTGCTGGGATTACTTCTTCAGGTTAAC CCAACAGAAGGCTCGAGTGCTGTTGACAGTGAGCGCGCAGTTATAATA TAAGTAGATCTAGTGAAGCCACAGATGTAGATCTACTTATGTTATAACT GCGGTGCCTACTGCCTCGGAGAATTCAAGGGGCTACTTTAGGAGCAAT TATCTTGTTTACTAAAACTGAATACCTTGCTATCTCTTTGATACATTTT TACAAAGCTGAATTAAAATGGTATAAATTAAATCACTTTTTTCAATTG TTTCCTTTTTTTTGCTCAGGGGTCGACGTTGACTACAGCCAAGGT-3' |

The invention claimed is:

1. A cellular biosensor system comprising:
at least one first gene comprising:
  1.1 a first gene promoter sequence,
  1.2 a sequence encoding a transcriptional activator protein that is operably linked to the first gene promoter sequence,
  1.3 at least one target site-1 for one or more chemical inputs,
  wherein upon chemical input binding, the target site-1 is capable of inhibiting or repressing the expression of the transcriptional activator that is operably linked to the first gene promoter sequence;
at least one second gene comprising:
  2.1 a second gene promoter inducible by the transcriptional activator protein, and that is operably linked to either,
    (i) a sequence encoding a transcriptional repressor and at least one target site-2 for one or more chemical inputs, and/or
    (ii) one or more repressor sequences encoding at least one repressor microRNA,
  wherein:
    upon chemical input binding, the target site-2 is capable of inhibiting or repressing the expression of the transcriptional repressor and,
    the transcriptional repressor and/or the at least one repressor microRNA inhibits or represses the expression of at least one output sequence by repressing transcription from a third gene promoter sequence;
at least one third gene comprising:
  3.1 the third gene promoter sequence that is repressible by the transcriptional repressor of the second gene when the second gene comprises the transcriptional repressor,
  3.2 at least one output sequence,
  3.3 at least one sequence(s) enabling gene rearrangement in the presence of at least one site-specific recombinase,
  3.4 at least one micro RNA microRNA target site for the at least one repressor microRNA, if when the second gene comprises one or more repressor sequences encoding at least one repressor microRNA,
  wherein upon gene rearrangement in the presence of at least one site-specific recombinase, the third gene promoter is operably linked to the output sequence such that the output sequence is expressed; and
at least one fourth gene comprising:
  4.1 at least one fourth gene promoter, and
  4.2 a sequence encoding the site-specific recombinase that enables gene rearrangement in the third gene that is operably linked to the fourth gene promoter.

2. The cellular biosensor system of claim 1, wherein the fourth gene includes at least one sequence enabling gene rearrangement in the presence of at least one further site-specific recombinase, wherein upon gene rearrangement in the presence of the at least one further site-specific recombinase, the fourth gene promoter is operably linked to the coding sequence of the site-specific recombinase.

3. The cellular biosensor system of claim 1, wherein at least two of (i) the at least one target site for one or more chemical inputs in the first gene, and (ii) the at least one target site for one or more chemical inputs in the second gene, are identical.

4. The cellular biosensor system of claim 1, wherein the one or more repressor sequences encoding at least one repressor microRNA in the second gene is intronic and requires splicing for encoding functional repressor microRNA.

5. The cellular biosensor system of claim 1, wherein the first gene promoter sequence of the first gene is mammalian cell promoter Elongation factor 1 alpha or the promoter from cytomegalovirus.

6. The cellular biosensor system of claim 1, wherein the transcriptional activator of the first gene is (i) an artificial eukaryotic transactivator or a tetracycline-dependent transcriptional activator, or (ii) a natural eukaryotic activator or Sp1.

7. The cellular biosensor system of claim 1, wherein the one or more chemical inputs for at least one target site in the first gene, and the second gene is an inhibitor or repressor of gene expression or gene product activity selected from the group consisting of endogenously expressed microRNA molecules, artificially expressed microRNA molecules, a combination of endogenously expressed and artificially expressed microRNA molecules, an antibiotic that interferes with transcription factor binding, a chemical inhibitor, a chemical interacting with a riboswitch, a small non-coding RNA, and a (poly)peptide.

8. The cellular biosensor system of claim 1, wherein at least one of the one or more chemical inputs for at least one target site in the first gene, and the second gene is a nucleotide sequence or a microRNA, and one or more of the at least one target site is at least partially complementary to the input nucleotide sequence.

9. The cellular biosensor system of claim 8, wherein at least one of the target sites in the first gene, and the second gene comprises a number of identical repeats that are at least partially complementary to the input nucleotide sequence.

10. The cellular biosensor system of claim 1, wherein at least one of the one or more chemical inputs for at least one target site in the first gene, and the second gene is a non-microRNA input interacting with the target site or a riboswitch target sequence that can be inhibited by a small molecule-input, an RNA-input, or a protein-input.

11. The cellular biosensor system of claim 1, wherein at least one target site in the first gene, and the second gene is embedded in the 3'-untranslated region or the 5'-untranslated region of these genes, or overlaps with the sequence encoding the transcriptional activator of the first gene, or overlaps with the transcriptional repressor sequence of the second gene.

12. The cellular biosensor system of claim 1, wherein at least one or more chemical inputs for the at least one target site in the first gene, and the second gene interact with the genes on the post-transcriptional mRNA level.

13. The cellular biosensor system of claim 1, wherein the second gene promoter of the second gene is a pTRE promoter.

14. The cellular biosensor system of claim 1, wherein the transcriptional repressor of the second gene is a repressor selected from the group consisting of a (poly)peptide repressor, a non-coding RNA repressor, a combination of different repressors, a combination of a protein repressor and a non-coding RNA repressor, a combination of two repressor proteins linked via a peptide linker, an internal ribosome entry site (IRES), and Lac1.

15. The cellular biosensor system of claim 1, wherein the sequence encoding the transcriptional repressor of the second gene is embedded in the 3'-untranslated region or the 5'-untranslated region of the second gene, or overlaps with the coding sequence of the transcriptional repressor sequence of the second gene.

16. The cellular biosensor system of claim 1, wherein the output sequence of the third gene encodes a product selected from the group consisting of mRNA, non-coding RNA, microRNA, (poly)peptides, fluorescent proteins, green fluorescent protein (GFP), DsRed, cell surface proteins, toxic proteins, apoptotic proteins, transcriptional regulators, and site-specific recombinases.

17. The cellular biosensor system of claim 1, wherein the at least one sequence(s) enabling gene rearrangement controls the orientation and/or specific genetic sequence of at least one of the third gene promoter or the at least one output sequence in the presence of at least one site-specific recombinase.

18. The cellular biosensor system of claim 1, wherein the at least one sequence(s) enabling gene rearrangement is the FLeX switch that is based on (i) LoxP and Lox2272 sites and Cre recombinase or based on (ii) FRT and F3 sites and Flp recombinase.

19. The cellular biosensor system of claim 1, wherein when the second gene comprises one or more repressor sequences encoding at least one repressor microRNA, the at least one microRNA target site in the third gene for the at least one repressor microRNA of the second gene is embedded in the 3'-untranslated region of the third gene, the 5'-untranslated region of the third gene, or overlaps with the at least one output sequence of the third gene.

20. The cellular biosensor system of claim 1, wherein at least one microRNA target site in the third gene is at least partially complementary to the at least one repressor microRNA of the second gene.

21. The cellular biosensor system of claim 1, wherein the at least one fourth gene promoter sequence of the fourth gene is mammalian cell promoter Elongation factor 1 alpha.

22. The cellular biosensor system of claim 1, wherein the site-specific recombinase encoded by the fourth gene is selected from the group consisting of Cre, Flp and PhiC31.

23. The cellular biosensor system of claim 1, wherein the fourth gene comprises at least one rearrangement sequence(s) enabling gene rearrangement in the presence of at least one further site-specific recombinase, and wherein the rearrangement sequence(s) in the fourth gene-controls the orientation and/or specific genetic sequence of: (i) the fourth gene promoter, (ii) the sequence encoding the site-specific recombinase enabling gene rearrangement in the third gene, or (iii) the fourth gene promoter, and the sequence encoding the site-specific recombinase enabling gene rearrangement in the third gene.

24. The cellular biosensor system of claim 23, further comprising a fifth gene encoding the further site-specific recombinase that controls genetic rearrangement in the fourth gene.

25. A transgenic animal model comprising the cellular biosensor system of claim 1.

26. The cellular biosensor system of claim 1, wherein the at least one fourth gene includes:
   4.3 at least one target site-3 for one or more chemical inputs;
   4.4 at least one microRNA target site for the at least one repressor microRNA when the second gene comprises one or more repressor sequences encoding at least one repressor microRNA; or
   4.4 both 4.3 and 4.4.

27. The cellular biosensor system of claim 26, wherein when the second gene comprises one or more repressor sequences encoding at least one repressor microRNA, the at least one microRNA target site in the fourth gene for the at least one repressor microRNA of the second gene is embedded in the 3'-untranslated region of the fourth gene, the 5'-untranslated region of the fourth gene, or overlaps with the sequence encoding the site-specific recombinase enabling gene rearrangement in the third gene.

28. The cellular biosensor system of claim 26, wherein at least two of (i) the at least one target site for one or more chemical inputs in the first gene, (ii) the at least one target site for one or more chemical inputs in the second gene, and (iii) the at least one target site for one or more chemical inputs in the fourth gene, are identical.

29. The cellular biosensor system of claim 26, wherein the one or more chemical inputs for at least one target site in the fourth gene is an inhibitor or repressor of gene expression or gene product activity selected from the group consisting of endogenously expressed microRNA molecules, artificially expressed microRNA molecules, a combination of endogenously expressed and artificially expressed microRNA molecules, an antibiotic that interferes with transcription factor binding, a chemical inhibitor, a chemical interacting with a riboswitch, a small non-coding RNA, and a (poly)peptide.

30. The cellular biosensor system of claim 26, wherein at least one of the one or more chemical inputs for at least one target site in the fourth gene is a nucleotide sequence or a microRNA, and one or more of the at least one target site is at least partially complementary to the input nucleotide sequence.

31. The cellular biosensor system of claim 26, wherein at least one of the target sites in the fourth gene comprises a number of identical repeats that are at least partially complementary to the input nucleotide sequence.

32. The cellular biosensor system of claim 26, wherein at least one of the one or more chemical inputs for at least one target site in the fourth gene is a non-microRNA input interacting with the target site or a riboswitch target sequence that can be inhibited by a small molecule-input, an RNA-input, or a protein-input.

33. The cellular biosensor system of claim 26, wherein at least one target site in the fourth gene is embedded in the 3'-untranslated region or the 5'-untranslated region of these genes, or overlaps with the sequence encoding the transcriptional activator of the first gene, or overlaps with the transcriptional repressor sequence of the second gene.

34. The cellular biosensor system of claim 26, wherein at least one or more chemical inputs for the at least one target site in the third gene interact with the genes (1) on the post-transcriptional mRNA level.

35. A cellular biosensor system consisting of:
at least one first gene consisting of:
a first gene promoter sequence,
a sequence encoding a transcriptional activator protein operably linked to the first gene promoter sequence, and
at least one target site-1 for one or more chemical inputs,
wherein upon chemical input binding, the target site-1 is capable of inhibiting or repressing the expression of the transcriptional activator protein coding sequence operably linked to the first gene promoter sequence;
at least one second gene consisting of:
a second gene promoter inducible by the transcriptional activator protein, and that is operably linked to one or more repressor sequences encoding at least one repressor microRNA,
wherein:
the at least one repressor microRNA is capable of inhibiting or repressing the expression of at least one output sequence by repressing transcription from a third gene promoter sequence; and
at least one third gene consisting of:
the third gene promoter sequence,
at least one output sequence, and
at least one microRNA target site for the at least one repressor microRNA.

36. The cellular biosensor system of claim 35, wherein two or more of the at least one target site for one or more chemical inputs in the first gene are identical.

37. The cellular biosensor system of claim 35, wherein the one or more chemical inputs for at least one target site in the first gene is an inhibitor or repressor of gene expression or gene product activity selected from the group consisting of endogenously expressed microRNA molecules, artificially expressed microRNA molecules, a combination of endogenously expressed and artificially expressed microRNA molecules, an antibiotic that interferes with transcription factor binding, a chemical inhibitor, a chemical interacting with a riboswitch, a small non-coding RNA, and a (poly)peptide.

38. The cellular biosensor of claim 35, wherein the second gene further consists of at least one target site-2 for one or more chemical inputs, and upon chemical input binding, the target site-2 is capable of inhibiting or repressing the expression of the at least one repressor microRNA.

39. The cellular biosensor of claim 38, wherein the one or more chemical inputs for at least one target site-2 in the second gene is an inhibitor or repressor of gene expression or gene product activity selected from the group consisting of endogenously expressed microRNA molecules, artificially expressed microRNA molecules, a combination of endogenously expressed and artificially expressed microRNA molecules, an antibiotic that interferes with transcription factor binding, a chemical inhibitor, a chemical interacting with a riboswitch, a small non-coding RNA, and a (poly)peptide.

40. The cellular biosensor system of claim 38, wherein two or more of (i) the at least one target site for one or more chemical inputs in the first gene, and (ii) the at least one target site for one or more chemical inputs in the second gene, are identical.

* * * * *